(12) United States Patent
Eggink et al.

(10) Patent No.: US 10,350,260 B2
(45) Date of Patent: Jul. 16, 2019

(54) COMPOSITIONS AND METHODS FOR TREATING CANCER AND PERSISTENT VIRAL INFECTIONS

(71) Applicant: SUSAVION BIOSCIENCES, INC., Tempe, AZ (US)

(72) Inventors: Laura L. Eggink, Scottsdale, AZ (US); J. Kenneth Hoober, Phoenix, AZ (US)

(73) Assignee: Susavion Biosciences, Inc., Tempe, AZ (US)

( * ) Notice: Subject to any disclaimer, the term of this patent is extended or adjusted under 35 U.S.C. 154(b) by 0 days.

(21) Appl. No.: 15/569,753

(22) PCT Filed: Jul. 8, 2015

(86) PCT No.: PCT/US2015/039555
§ 371 (c)(1),
(2) Date: Oct. 26, 2017

(87) PCT Pub. No.: WO2016/175878
PCT Pub. Date: Nov. 3, 2016

(65) Prior Publication Data
US 2018/0140657 A1    May 24, 2018

Related U.S. Application Data

(63) Continuation-in-part of application No. 14/697,240, filed on Apr. 27, 2015, now abandoned.

(51) Int. Cl.
*A61K 38/08* (2019.01)
*A61K 39/395* (2006.01)
(Continued)

(52) U.S. Cl.
CPC .............. *A61K 38/08* (2013.01); *A61K 45/05* (2013.01); *A61P 31/12* (2018.01); *A61P 35/00* (2018.01);
(Continued)

(58) Field of Classification Search
CPC .. A61K 38/08; A61K 45/05; A61K 2039/572; A61K 2039/575; C07K 7/06
See application file for complete search history.

(56) References Cited

U.S. PATENT DOCUMENTS 7,811,995 B2 * 10/2010 Eggink ................ C07K 14/001
  514/19.3
7,838,497 B2  11/2010 Eggink et al.
(Continued)

FOREIGN PATENT DOCUMENTS

WO    WO-2013096829 A2 *  6/2013  ............. A61K 38/10

OTHER PUBLICATIONS

Oppenheim, Joost J., "IL-2: More Than a T Cell Growth Factor", The Journal of Immunology, 179(3):1413-1414 (Aug. 1, 2007).
(Continued)

*Primary Examiner* — Jeffrey E. Russel
(74) *Attorney, Agent, or Firm* — Rodney J. Fuller; Booth Udall Fuller, PLC

(57) ABSTRACT

The methods and compounds disclosed herein are useful in treating a subject having cancer or a viral infection by modulating the innate and adaptive immune systems typically by both inhibiting the function of inhibitory receptors and enhancing activity of activating receptors. Preferred therapeutic compositions comprise a carrier; at least one agent selected from the group consisting of: an anti-inflammatory agent, a cytotoxic T cell proliferation agent, or a NK cell proliferation agent; and a therapeutic peptide of the invention. In certain embodiments the compositions further include a second therapeutic peptide and/or an immunoglobulin admixed therewith in an amount sufficient to enhance passive immunoprotection in the subject.

24 Claims, 13 Drawing Sheets
Specification includes a Sequence Listing.

(51) Int. Cl.
  *A61P 35/00* (2006.01)
  *A61P 31/12* (2006.01)
  *A61P 37/02* (2006.01)
  *A61K 45/00* (2006.01)
  *A61K 45/06* (2006.01)
  *A61K 39/00* (2006.01)

(52) U.S. Cl.
  CPC ............ *A61P 37/02* (2018.01); *A61K 39/395* (2013.01); *A61K 45/06* (2013.01); *A61K 2039/572* (2013.01); *A61K 2039/575* (2013.01); *C12N 2740/16034* (2013.01); *C12N 2740/16088* (2013.01)

(56) References Cited

U.S. PATENT DOCUMENTS

| | | | | |
|---|---|---|---|---|
| 2005/0143347 | A1* | 6/2005 | Boderke | A61K 31/195 514/78 |
| 2007/0014765 | A1* | 1/2007 | Elias | A61K 38/2013 424/85.2 |
| 2007/0048394 | A1* | 3/2007 | Yang | A61K 36/28 424/764 |
| 2007/0166279 | A1* | 7/2007 | Talor | A61K 38/191 424/85.1 |
| 2009/0041793 | A1* | 2/2009 | Eggink | C07K 14/57 424/185.1 |
| 2010/0076072 | A1* | 3/2010 | Cook-Mills | A61K 31/355 514/458 |
| 2010/0285003 | A1 | 11/2010 | Eggink et al. | |
| 2010/0286040 | A1* | 11/2010 | Eggink | C07K 7/06 514/7.6 |
| 2013/0165339 | A1* | 6/2013 | Tan | G01N 33/564 506/9 |

OTHER PUBLICATIONS

Ohshio, Y. et al., "Cancer-associated fibroblast-targeted strategy enhances antitumor immune responses in dendritic cell-based vaccine", Cancer Sci., 106(2):134-142 (Abstract Only) (Feb. 2015).

* cited by examiner

COMPOSITIONS AND METHODS FOR TREATING CANCER AND PERSISTENT VIRAL INFECTIONS

CROSS REFERENCE TO RELATED APPLICATIONS

This application is the U.S. National Stage of International Application No. PCT/US2015/039555, filed on Jul. 8, 2015, which is a continuation-in-part of and claims priority to U.S. patent application Ser. No. 14/697,240 filed on Apr. 27, 2015 (published as 20150299255), the contents of each of which are incorporated herein by reference in their entireties.

INCORPORATION-BY-REFERENCE OF MATERIAL ELECTRONICALLY FILED

Incorporated by reference in its entirety herein is a computer-readable amino acid sequence listing identified as follows: One 2,722 byte ASCII (text) file named "Seq_List_ST25.txt" submitted on Mar. 11, 2019.

FIELD OF THE INVENTION

The present invention is directed to therapeutic peptides and their uses in modulating the innate and adaptive immune systems in a subject for treatment of infectious diseases and cancers.

BACKGROUND

Viral infections pose challenges for effective treatment. While an antiviral treatment may appear to treat the initial acute infection, physical symptoms of infection often return later as persistent infections. A common characteristic of persistent infections is the virus' ability to successfully modulate the immune response to avoid specific and non-specific immune defenses. In essence, persistent viral infections are immunosuppressive diseases. In general, the course of these diseases is moderated by the strength of the immune system. Persistent viral infections are also highly correlated with the development of cancer.

HIV-1 is an example of a virus that causes persistent infections. HIV is perhaps the most widely known of the viruses that cause immunosuppressive diseases. Although the immune system effectively produces antibodies against these viruses in the acute stage of the infection, the antibodies are largely non-neutralizing and allow the infection to progress to the chronic and eventually fatal stages. Moreover, the cytolytic components of the immune system fail to destroy infected cells even though the cells express pathogen-induced cell-surface antigens [1]. The primary therapy against such infections is daily administration of a combination of anti-retroviral drugs that inhibit viral replication after entry into the cell and subsequent maturation. The most commonly used are nucleoside reverse transcriptase inhibitors, non-nucleoside reverse transcriptase inhibitors, integrase inhibitors, and protease inhibitors that block enzymatic processing of viral products. These drugs effectively inhibit replication of the virus inside an infected cell and reduce viral load in the blood to undetectable levels [2,3].

A particularly confounding aspect of infections by these viruses is the establishment of latent reservoirs in which the integrated provirus stage can remain dormant for long periods of time. Consequently, the virus cannot be completely cleared from an infected individual by current treatments. Upon discontinuation of anti-retroviral treatment, these reservoirs are activated and the virus "rebounds" to pretreatment levels within a few weeks [3,4]. The question of whether the provirus is indeed dormant or simply replicates at a very low level has not been completely resolved. Often the immune system maintains suppression of viral replication but fails to maintain health when the immune system is compromised.

A defining characteristic of acquired immunodeficiency syndrome (AIDS) is the development of Kaposi sarcoma (KS), a type of cancer that affects cells lining the lymph and blood vessels. KS is caused by herpes virus in immunocompromised subjects.

Like HIV, cytomegalovirus (CMV) cause persistent infections associated with the immune system. CMV, however, is dormant in health individuals and generally becomes active when the immune system is compromised. The antiviral drug ganciclovir, a viral DNA polymerase inhibitor, is commonly used to treat acute cytomegalovirus (CMV) infections. Human CMV has also been found to play a role in the development of cancer through oncomodulation, e.g., enabling cancer cells to evade immune recognitions [44].

Chronic viral hepatitis is the most common risk factor worldwide for liver cancer. Like HIV, Hepatitis C virus (HCV) is a RNA virus and is more likely to result in chronic infection than hepatitis B virus (HBV). Recent advances in the treatment of HCV involve development of protease inhibitors that act in a similar manner as those used to treat HIV-1 infections [5]. For HCV, the protease inhibitors are added to the currently accepted drug regime of pegylated interferon-alpha and ribavirin.

About one-third of the world's population has evidence of a hepatitis B infection, either current or past, which is more than HIV and HCV infections combined [6]. Most healthy adults raise an effective immune response against hepatitis B virus (HBV), but the effectiveness of the immune defense is dependent upon the activity of natural killer (NK) cells [6]. NK T cells contribute to resolution of a HBV infection, with the NKG2D receptor playing a key role [6]. HBV establishes a chronic infection, and although infected cells express the hepatitis B surface antigen (HBsAg), the immune system is unable to prevent progression of the infection. Long term continuing virus replication leads to progression to cirrhosis and hepatocellular carcinoma [6-8]. Infection by HBV is the leading cause of hepatocellular carcinoma. Approximately 662,000 deaths occur worldwide each year, with roughly half of them in China [9].

A potentially powerful therapeutic approach for these persistent viral infections and immunosuppressive diseases is a combination of drugs with antiviral activity, in particular those that bind to NKG2D, and those with strong anticancer activity that promote induction of proliferation of activated cells of the innate and adaptive immune system.

An Alternative Approach to Therapy

In contrast to therapeutic approaches aimed at prevention or control of disease by directly inhibiting a step in the viral replication cycle, as described above, or by the use of highly toxic cytotoxic chemotherapeutic drugs for cancer treatment, reactivation of patients' immune system is an alternative therapy that holds promise for restoring health and productivity to an infected patient in a practical, cost-effective manner. This approach provides a general defense against diseases rather than a pathogen-specific treatment. As a result, an intense interest in immunotherapy, as indicated by the development of cytokine and monoclonal antibody treatments, is leading to products that can stimulate or inhibit the immune system.

The role of cytokines in the inhibition of HIV infectivity, particularly interleukin-16 (IL-16), interleukin-8 (IL-8) and RANTES (Regulated upon Activation, Normal T-cell Expressed, and Secreted; also known as CCL5), is very important. Cytokines such as IL-16, IL-8 and RANTES, which have overlapping and complementary functions, can act to attenuate viral infection by competing with viral binding with the receptors and by interfering with viral entry into cells by down-regulating the receptors required for entry. Other cytokines such as interferons (e.g., IFN-α. and IFN-γ) act to reduce viral load by activating intracellular anti-viral enzymes and also by stimulating antibody-mediated phagocytosis. These cytokines have also been shown to be effective in the acute stage of HBV infection [6].

Interleukins (IL's) and interferons (IFN's) are potent cellular stimulants that are released from a variety of cells in response to insult or injury. Consequently, these proteins have attracted intense interest as therapeutic agents. IL-16 is a natural ligand of CD4 and should compete with virus for binding to T cells. IL-21 is required to avoid depletion of $CD8^+$ T cells and also essential to maintain immunity and resolve persistent viral infections [10-12]. Similar to general stimulants such as lipopolysaccharide (LPS), however, IL's and IFN's induce release of inflammatory cytokines. Therefore, when given at higher than normal endogenous concentrations, they often have substantial adverse effects, which can be life threatening and may require inpatient treatment facilities. Similarly, levels of TNF-α, IL-1β and IL-6 are directly correlated with the probability of death in humans. Moreover, production of recombinant IL's and IFN's and their application are very costly. Even lower-dosage immunostimulant treatments developed for out-patient use have lower success rates and are not suitable in some situations such as, for example, to extend remission from cancer therapy or control a disease such as HIV at a chronic level. In view of this, it appears that exogenous therapeutic agents such as large, intact cytokine molecules are not well suited for general therapeutic use.

Usually, infections are cleared by the immune system through (i) internalization of the pathogen and presentation of antigens to T and B cells by dendritic cells (DCs), (ii) generation of antibodies by B cells, (iii) lysis of pathogen-infected cells by NK cells and $CD8^+$ cytotoxic T lymphocytes (CTL), and/or (iv) destruction of the virus or cancer cell by antibody-mediated phagocytosis. While neutralizing antibody responses are subject to pathogen escape, many non-neutralizing antibodies that nevertheless bind the pathogen are present in infected patients. Restoration of immune effector cell functions, in particular phagocytic activity, which can recognize the resulting antigen-antibody complexes and destroy the complexes by antibody (Fc)-mediated phagocytosis, may be applicable to the clearance of infections in general.

The cell types that have significant involvement in viral infections in addition to phagocytic cells are in particular, two subsets of the T cell population ($CD3^+$ and $CD8^+$), NK cells ($CD56^+$) and CTLs (CD8+). These cells are able to kill virus-infected cells and cancer cells by antibody-dependent cellular cytotoxicity (ADCC) in addition to an ability to directly lyse infected cells. NK cells are an integral component of the innate immune system and are primarily responsible for killing virus-infected and cancer cells. NK cells and CTL kill their targets mainly by releasing cytotoxic molecules such as perforin, granzymes and granlysin, which are contained in intracellular granules. These molecules are released when these cells make contact with target cells that contain antigens on the surface of viral infected or cancer cells to which antibodies bind. Activated NK cells also release cytokines and chemokines such as IFN-γ that activates macrophages and drives differentiation of $CD4^+$ T cells into type 1 (Th1) cells [11,12].

Information relevant to attempts to address one or more of these problems can be found in the following references: U.S. Patent Publication No. 2007/0003542; U.S. Patent Publication No. 2006/0269519; U.S. Patent Publication No. 2004/0248192; P. W. Latham, 1999; Fatkenheuer et al., 2005; Stover et al., 2006; Cohen, 2007; GlaxoSmithKline, 2005a and GlaxoSmithKline, 2005b. Each one of these treatments referred to in these references, however, suffers from one or more of the following disadvantages:

1. the size or composition of the agent provides significant challenges to cost-effective synthesis and purification;
2. the agent is specific for particular pathogen and/or cell type, rendering them unsuitable for general therapeutic use;
3. treatment with the agent induces clinically deleterious side effects that can be life-threatening, such as inflammation or hepatotoxicity, and require inpatient treatment facilities;
4. termination of treatment is followed soon thereafter by an increased systemic viral load;
5. long term exposure to agent often leads to treatment-resistant pathogens;
6. lower-dosage treatments developed for out-patient use have lower success rates and are not suitable in some situations;
7. treatment is ineffective, impractical, or cost-prohibitive for a large proportion of patients;
8. development of therapeutic antibodies require considerable medical infrastructure;
9. treatment such as vaccines may be appropriate to prevent infection but not to treat those already infected and who have a suppressed immune system;
10. no beneficial synergy between the immunogenic response induced and the effects of other endogenous immunoregulators;
11. agent inhibits the release of inhibitory cytokines that suppress release of beneficial cytokines, an indirect treatment; and
12. agent acts to restore baseline cytokine levels to balance responses of the immune system rather than promoting activation of phagocytes.

Many of these therapeutic protocols also become ineffective with time because mutation of the pathogen allows it to escape the treatment. Moreover, any immunosuppression that accompanies the disease attenuates the ability of the innate and adaptive immune systems to respond to antigenic changes and thereby keep the infection under control.

The immune system in individuals infected with a pathogenic agents such as HIV-1 or HBV initiate a defense response by production of antibodies. Even though the virus may mutate at one or a few sites and thereby escape the neutralizing activity of antibodies, endogenously produced non-neutralizing antibodies are usually polyclonal and may still bind the virus. The presence of anti-viral antibodies is often used as a diagnostic test for infection. During the course of the disease, the cellular components of the innate and adaptive immune response then become absent or quiescent. When the immune defense mechanisms reach a sufficiently low level, viral replication is not held in check and rapidly leads to a final stage of the disease. However, even at this late stage, patients can be rescued from death by aggressive therapy. Therefore, an agent that reactivates cells of the immune system, in particular phagocytes and NK cells, will likely restore an immune defense against progression of the disease.

Not only is it essential to overcome the suppressive mechanisms of the pathogen, it is also important to modulate the host's natural mechanism that suppress the immune system. Therapeutic agents that activate/reactivate the immune system show particular promise in this regard, including cytokines and immunomodulators, although therapies based on exogenous agents such as large, intact cytokine molecules are not generally well suited for therapeutic use. Peptides, however, are often much more suitable therapeutic agents than large polypeptides or proteins. Peptides can, for example, be designed to induce one or more particular desired effects in vitro or in vivo, often without concomitantly inducing deleterious effects, and can usually be synthesized in a cost effective manner.

The development of this technology is applicable to diseases caused by viruses, bacteria, fungi and cancers.

SUMMARY OF THE INVENTION

The present invention is directed to methods of treating an immunocompromised subject, the method comprising: administering to the immunocompromised subject a composition comprising a therapeutic peptide or a multivalent structured polypeptide comprising multiple copies of the therapeutic peptide, the therapeutic peptide consisting of 5 to 8 amino acids and selected from the group consisting of:
VGGGS (SEQ ID NO:1) and
X1-X2-X3-X4-X5-X6-X7-X8,
wherein:
X1 is selected from the group consisting of H and N;
X2 is selected from the group consisting of P and Q;
X3 is selected from the group consisting of S and H;
X4 is selected from the group consisting of H, T, and L;
X5 is selected from the group consisting of P and K, or is absent;
X6 is selected from the group consisting of R, L and S, or is absent;
X7 is selected from the group consisting of S and L, or is absent; and
X8 is G, or is absent;
wherein the therapeutic peptide or multivalent structured polypeptide is in an amount sufficient to increase, activate, and/or stimulate proliferation of immune cells in the subject.

The present invention is also directed to methods of treating a subject having cancer and/or a viral infection: the method comprising administering to the subject with cancer and/or a viral infection a therapeutic peptide or a multivalent structured polypeptide comprising multiple copies of the therapeutic peptide, the therapeutic peptide consisting of 5 to 8 amino acids and selected from the group consisting of:
VGGGS (SEQ ID NO:1) and
X1-X2-X3-X4-X5-X6-X7-X8,
wherein:
X1 is selected from the group consisting of H and N;
X2 is selected from the group consisting of P and Q;
X3 is selected from the group consisting of S and H;
X4 is selected from the group consisting of H, T, and L;
X5 is selected from the group consisting of P and K, or is absent;
X6 is selected from the group consisting of R, L and S, or is absent;
X7 is selected from the group consisting of S and L, or is absent; and
X8 is G, or is absent;
wherein the therapeutic peptide or multivalent structured polypeptide is in an amount sufficient to treat the cancer and/or virus by increasing proliferation of immune cells in the subject.

In certain specific embodiments of the aforementioned methods, therapeutic peptide may be selected from the group consisting of one or more of the following: VGGGS (SEQ ID NO:1), HPSLK (SEQ ID NO:2), NPSHPLSG (SEQ ID NO:3), NPSHPSLG (SEQ ID NO:4), and NQHTPR (SEQ ID NO:5). In some implementations, the subject may have a persistent viral infection, which may be selected from the group consisting of: an HIV/AIDS infection, a CMV infection, a HBV infection, and a HCV infection.

In a particular non-limiting embodiment, the invention is directed to a method of treating a subject having cancer by administering to the subject with cancer a therapeutic peptide or a multivalent structured polypeptide comprising multiple copies of the therapeutic peptide, wherein the therapeutic peptide is NQHTPR (SEQ ID NO:5), wherein the therapeutic peptide or multivalent structured polypeptide is in an amount sufficient to treat the cancer in the subject.

In one embodiment, the multivalent structured polypeptide is administered to the subject and is branched. In certain non-limiting aspects of the invention the therapeutic peptide or multivalent structured polypeptide administered to the subject stimulates proliferation of immune cells selected from the group consisting of macrophages; dendritic cells; natural killer cells; natural killer T cells; CD3+, CD4+ and CD8+ T cells; B cells; and combinations thereof.

In a specific embodiment, the therapeutic peptide or multivalent structured polypeptide is administered in an amount sufficient to induce antibody-mediated cellular cytotoxicity in the subject, preferably to increase the expression of at least one endogenous cytokine from lymphocytes elected from the group consisting of: IL-2, IL-4, IL-12, IL-16, IL-17, IL-21, TNF-β, IFN-γ and RANTES and/or decreases at least one endogenous cytokines elected from the group consisting of: IL-1α, IL-1β, IL-13, and TNF-α. In addition, the multivalent structured polypeptide induces rapid modifications of phosphorylated kinases involved in signal transduction to achieve these activities.

In certain implementations, the present method further comprises the step of determining (a) the level of immune cells in the immunocompromised subject before administering the composition; and (b) the level of immune cells in the immunocompromised subject after administering the composition. The levels of (a) and (b) may be determined with flow cytometry. Examples of preferred ratios of (b) to (a) is at least 2, at least 3, at least 4, or at least 5. Yet other aspects of the invention, the ratio of (b) to (a) is at least 1.5, at least 2, at least 2.5, at least 3, at least 3.5, at least 4, at least 4.5, or at least 5.

In some implementations of the present invention, the therapeutic peptide preferably functionally mimics a terminal sequence 5-acetylneuraminic acid-galactose on complex glycans or glycoproteins, the terminal sequence being linked α(2,3) or α(2,6). The therapeutic peptide preferably functionally mimics a terminal N-acetylgalactosamine or galactose on cell-surface glycoproteins. The therapeutic peptides are advantageously configured to bind to the receptor NKG2D and/or siglecs and function as modulators of the immune system by binding to receptors on B cells, DCs, NK cells, T cells, cytotoxic T cells and/or phagocytic cells. In addition, therapeutic peptides bind to receptors specific for N-acetylgalactosamine or galactose such as CLEC10a/

CD301 on immature DCs and macrophages, langerin on DCs and asialylglycoprotein receptor-1 on hepatic cells. In some embodiments, the therapeutic peptide or multivalent structured polypeptide activates the immune cells by binding to the inhibitory siglec receptors. In some embodiments, the therapeutic peptide or multivalent structured polypeptide activates the immune cells by binding to an activating receptor including NKG2D and/or CLEC10a.

The methods of the present invention may further comprise administering to the subject a second therapeutic peptide or a multivalent structured polypeptide comprising multiple copies of the second therapeutic peptide. The second therapeutic peptide consists of 5 to 8 amino acids and selected from the group consisting of:
VGGGS (SEQ ID NO:1); and

X1-X2-X3-X4-X5-X6-X7-X8, wherein
X1 is selected from the group consisting of H and N;
X2 is P;
X3 is S;
X4 is selected from the group consisting of H and L;
X5 is selected from the group consisting of P and K, or is absent;
X6 is selected from the group consisting of L and S, or is absent;
X7 is selected from the group consisting of S and L, or is absent; and
X8 is G, or is absent;

In some implementations, the second therapeutic peptide is selected from the group consisting of: VGGGS (SEQ ID NO:1), HPSLK (SEQ ID NO:2), NPSHPLSG (SEQ ID NO:3), and NPSHPSLG (SEQ ID NO:4). In some aspects, the multivalent structured polypeptide comprising the second therapeutic peptide is administered to the subject, wherein the multivalent structured polypeptide is branched. In some implementations, the second therapeutic peptide functionally mimics a terminal sequence 5-acetylneuraminic acid-galactose or N-acetylgalactosamine on complex glycans, the terminal sequence being linked α(2,3) or α(2,6) or terminal sugars such as N-acetylgalactosamine or galactose.

The therapeutic peptide or multivalent structured polypeptide of the aforementioned methods may be in a composition comprising a carrier. In some embodiments, the composition may further comprises at least one agent selected from the group consisting of: an anti-inflammatory agent, a cytotoxic T cell proliferation agent, or a NK cell proliferation agent; and a therapeutic peptide or a multivalent structured polypeptides of the invention. Such compositions may further comprise an antibody preparation admixed in an amount sufficient to enhance antibody-mediated cellular cytotoxicity in a subject; or an immunoglobulin admixed therewith in an amount sufficient to enhance passive immunoprotection in the subject Therapeutic compositions are also contemplated in the present invention. The therapeutic compositions of the present invention comprise a carrier, a therapeutic peptide or a multivalent structured polypeptide comprising multiple copies of the therapeutic peptide, wherein the therapeutic peptide is NQHTPR (SEQ ID NO:5), wherein the therapeutic peptide or multivalent structured polypeptide is in an amount sufficient to treat the cancer in a subject; and at least one agent selected from the group consisting of: a B cell proliferation agent, a cytotoxic T cell proliferation agent, or a NK cell proliferation agent. The composition may further comprise an antibody preparation admixed in an amount sufficient to enhance antibody-mediated cellular cytotoxicity or further comprises an immunoglobulin admixed with the polypeptide composition in an amount sufficient to enhance passive immunoprotection.

In some embodiments, the therapeutic composition further comprises a second therapeutic peptide or a multivalent structured polypeptide comprising multiple copies of the second therapeutic peptide. The second therapeutic peptide consists of 5 to 8 amino acids and selected from the group consisting of:
VGGGS (SEQ ID NO:1); and

X1-X2-X3-X4-X5-X6-X7-X8, wherein
X1 is selected from the group consisting of H and N;
X2 is P;
X3 is S;
X4 is selected from the group consisting of H and L;
X5 is selected from the group consisting of P and K, or is absent;
X6 is selected from the group consisting of L and S, or is absent;
X7 is selected from the group consisting of S and L, or is absent; and
X8 is G, or is absent;

In some aspects, the second therapeutic peptide is selected from the group consisting of: VGGGS (SEQ ID NO:1), HPSLK (SEQ ID NO:2), NPSHPLSG (SEQ ID NO:3), and NPSHPSLG (SEQ ID NO:4). In some implementations, the multivalent structured polypeptide comprising the second therapeutic peptide is administered to the subject, wherein the multivalent structured polypeptide is branched.

BRIEF DESCRIPTION OF THE DRAWINGS

FIG. 1 illustrates a model of monovalent SVH1C (SEQ ID NO:3, space-filled structure) docked in the glycan-binding site of the receptor Siglec-5 (accession no. 2ZG1), predicted binding energy, ΔG'=−47 kJ/mol. The predicted binding energy suggests strong interaction with the receptor, with a $K_D$=~$1\times10^{-8}$ M.

FIG. 2 illustrates a model of monovalent SVH1C (SEQ ID NO:3, space-filled structure) docked in the ligand binding site of the receptor NKG2D (accession no. 1MPU). The predicted binding energy for NPSHPLSG (SEQ ID NO:3) was ΔG'=−40 kJ/mol, which corresponds to a $K_D$=~$1\times10^{-7}$ M.

FIG. 3 illustrates a model of monovalent SV6D (SEQ ID NO:5, space filled structure) docked in the ligand binding site of the receptor asialylglycoprotein receptor-1 (ASGPR-1) (accession no. 1DV8), a protein homologous to CLEC10a that is highly specific for N-acetylgalactosamine. The predicted binding energy was ΔG'=−40 kJ/mol, which corresponds to a $K_D$=~$1\times10^{-7}$ M.

FIG. 4 illustrates a model of the final design of the peptide. Four identical, active sequences (e.g., arms 1 and 2) were extended from a central core (4), composed of trilysineamide, by a linker sequence (3).

FIG. 5 demonstrates and shows the multivalent structure of SVH1C ([NPSHPLSGGGGS]4K3-NH2). N, asparagine; P, proline; S, serine; H, histidine; L, leucine; G, glycine; K, lysine. The molecular weight of the peptide is 4,593.9. A linker sequence (GGGS) (SEQ ID NO:6) extends the active sequence from the tri-lysine core.

FIG. 6 demonstrates and shows the multivalent structure of SV6D ([NQHTPRGGGS]4K3-NH2). N, asparagine; Q, glutamine; H, histidine; T, threonine; P, proline; R, arginine, G, glycine; S, serine; K, lysine. The molecular weight is 4,369.1. A linker sequence (GGGS) (SEQ ID NO:6) extends the active sequence from the tri-lysine core.

DETAILED DESCRIPTION OF THE PREFERRED EMBODIMENTS

Figure 1:
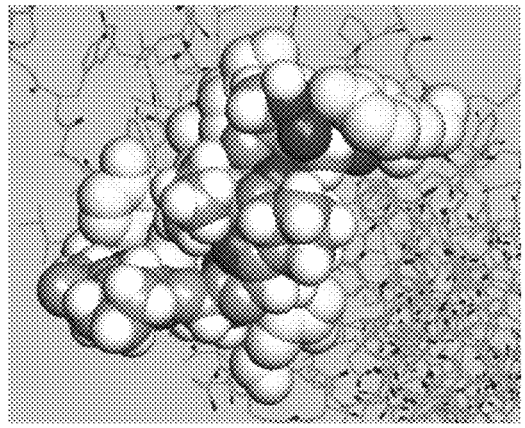
FIGS. 1-3 depict models of monovalent therapeutic peptides.

The present invention is directed to compositions and methods for activation and proliferation of macrophages, B cells, DCs, NK cells, T cells and/or CD8+ cytotoxic T lymphocytes. The compositions and methods involve the use of peptidic mimetics of glycan ligands of receptors that can overcome immunosuppression, produce antiviral activity, and/or anticancer activity.

Overcoming Immune System Suppression

Inhibitory mechanisms naturally maintain a balance within the immune system to prevent progression of an over-stimulated, deleterious immune response. Major components in these inhibitory mechanisms are cell-surface, lectin-type receptors of the siglec (sialic acid-binding immunoglobulin-like lectins) family [13,14]. The cytoplasmic domains of most siglecs contain ITIMs (immunoreceptor tyrosine-based inhibitory motifs) that when phosphorylated recruit tyrosine phosphatases such as SHP-1. Siglecs are abundant cell-surface proteins and bind to sialic acid residues on glycoprotein subunits of activating receptor complexes such as the B cell receptor (BCR). Siglec-associated SHP-1 then dephosphorylates (deactivates) the activating complexes, which suppresses immune functions [13-15].

Most cells of the immune system contain several siglecs [13-15]. A total of 14 siglecs is expressed in humans. As an example, the extensively studied Siglec-2 binds to sialic acid residues on BCR-associated proteins such as IgM, causes suppression of the activity of BCR in antigen recognition and antibody production [14,15]. Siglec-2 contains six tyrosine residues within its cytoplasmic domain, three of which are within three ITIMs, which are potentially phosphorylated. Sialosides with high affinity to Siglec-2 bind to the sialic acid-binding site of Siglec-2 and release it from the BCR complex [14,16]. Consequently, activation of the BCR complex is no longer attenuated and B cell activation ensues. It can be expected that similar suppression of other immune cells by siglecs is also relieved by binding of small molecules that inhibit the suppressive activity of these receptors. Whereas most siglecs express inhibitory functions, Siglec-14, -15 and -16 lack cytoplasmic ITIMs and serve activating functions in association with an adaptor protein DAP12, which contains an ITAM (immunoreceptor tyrosine-based activating motif) [13-15]. A compound that binds to multiple siglecs should provide a powerful mechanism to achieve multiple immune cell activation by decreasing the suppressive ability of siglecs while also increasing activating functions. An additional receptor that binds sialic acid-galactose sequences is the potent activating receptor, NKG2D, which is expressed on NK cells, γδ T cells and CD8+ cytotoxic T cells [17,18]. NKG2D also functions with cytoplasmic adaptor proteins DAP10 and DAP12 that contain ITAMs. One set of peptides described in this invention are mimetics of sialic acid-galactose sequences and bind with high avidity to these receptors [19].

The peptides of this invention that mimic sialic acid, such as NPSHPLSG (SEQ ID NO:3), have a dual function. Firstly, they bind to the inhibitory siglec receptors. Secondly, they also bind to the activating receptor, NKG2D. The siglecs, as inhibitory receptors that prevent excessive activation of the immune system, are 'checkpoints'. By binding to and inactivating these receptors, the peptides of this invention can be considered 'checkpoint inhibitors'. Concomitantly, by binding to activating receptors on the same cell, the peptides exert a strong stimulatory effect on these cells. Essential for this function is the much greater avidity of the peptides to the sialic acid-binding sites than natural, cell-based glycans. In fact, siglecs bind sialic acid-containing ligands with $K_D$ values in the low millimolar range, whereas the peptides bind with three orders of magnitude greater avidity, with $K_D$ values of 1 micromolar or less. Thus the peptides are well suited to provide therapeutic benefit.

Thus, interaction of peptides with lectin-type inhibitory receptors leads to activation of immune cells. These activities can be coupled with other peptides that bind to activating receptors and directly activate immune cells. Lectins are generally highly-specific, carbohydrate-binding proteins, and these receptors interact with ligands that contain sugar residues. Cells of the immune system express an extensive array of regulatory, C-type lectin cell-surface receptors [20,21]. A second set of peptides of this invention are mimetics of N-acetylgalactosamine (GalNAc) and galactose (Gal) and bind to receptors that lead to activation of immune cells. A receptor with this ligand specificity is the macrophage galactose-type lectin (MGL), a calcium-dependent (C-type) lectin also designated CLEC10a or CD301 [22]. Two forms of this receptor are expressed in the mouse, one that is specific for galactose (Gal, MGL1) and the second specific for GalNAc (MGL2). CLEC10a is expressed by macrophages and immature dendritic cells, which are the primary antigen-presenting cells (APCs). The lectin-type receptors on immune cells therefore present an entry into the immune system.

CLEC10a binds to a glycan on the ubiquitous phosphatase CD45 and attenuates its activity. The phosphatase activity of CD45 is required for lymphocyte activation [23]. Engaging CLEC10a with a peptide that binds with much higher avidity than the glycan on CD45 leads to cellular activation. Thus, CLEC10a is a strategic target for activation of immune cells. An extensive literature has demonstrated that targeting CLEC10a promotes internalization of antigens by DCs, presentation of antigens to CD4+ T cells and differentiation of IFNγ-producing CD4+ T cells [22,24]. Ligand binding to CLEC10a also results in enhanced antigen-specific, IFNγ-producing CD8+ T cell responses and tilts naïve CD4+ T cells towards Th1 cells, with increased proliferation of T cells. In addition, DCs mediate activation and proliferation of natural killer (NK) cells [25]. The phosphatase activity of CD45, a widely expressed and abundant cell surface protein, is required for lymphocyte activation and development [23]. Trans binding of CLEC10a on DCs to a GalNAc residue on CD45 on T cells results in T cell inhibition [26]. Introduction of a GalNAc-containing factor displaces CLEC10a from CD45 and allows dephosphorylation of inhibitory receptors and T cell activation [24]. CLEC10a is the likely receptor for the macrophage activating factor, a clinically potent anti-cancer derivative of serum group specific component-1 (Gc1) that contains a covalently-bound GalNAc. A hydrolase expressed by some cancer cells removes the GalNAc residue, thereby inactivating the protein [27]. These results suggested a critical role for receptors of GalNAc-containing ligands in regulation of immune cells and the treatment of cancer.

Current immunotherapy of cancer has focused on the use of monoclonal antibodies to bind to, and inhibit the activity of, inhibitory receptors on T cells such as PD-1 and CTLA-4. Antibodies have also been developed against a protein, PD-L1, that is highly expressed by cancer cells and acts as an activating ligand for PD-1. Combinations of these antibodies have proven to be very effective in treating certain types of cancer [28]. The antibodies are injected intravenously and cause significant toxic side-effects. Although the peptides of this invention interact with different inhibitory receptors, the overall result may be the same but simply be achieved through different mechanisms and with considerably less toxicity.

Peptidic Mimetics of Glycan Ligands of Receptors

An important component of immune system stimulation by the peptides is activation and proliferation of B cells, DCs, NK cells, T cells and CTL (cytotoxic T lymphocytes) in addition to activation of phagocytic cells. To this end, peptidic mimetics of the glycan 5-acetylneuraminic acid-galactose [Neu5Ac(α2,3)Gal and Neu5Ac(α2,6)Gal] were designed. These glycans bind to NKG2D, an important activating receptor on NK cells, γδ T cells and CD8+ cytotoxic T cells [18], and to the family of siglecs (sialic acid-binding Ig-like lectin) receptors that is present on most cells of the immune system and are generally inhibitory receptors [13-15]. Whereas identified endogenous ligands of NKG2D are several protein-based activating ligands [17, 29], binding of glycans should also activate these cells. Activation of phagocytes occurs by binding of peptides to siglecs or other receptors on these cells. The therapeutic peptides consist of a multivalent structure in which the arms consist of sequences only 9 to 12 amino acids long (including a linker sequence). The active sequences of the relevant peptides that were described previously [U.S. Pat. Nos. 7,811,995 and 8,496,942, incorporated by reference thereto] are VGGGS (SEQ ID NO:1), HPSLK (SEQ ID NO:2), NPSHPLSG (SEQ ID NO:3), and NPSHPSLG (SEQ ID NO:4). Preferably, the peptides are in substantially pure form. Typically it is desired that the peptides be at least 70%, more preferably at least 80%, and most preferably at least 95% pure by weight. In one embodiment the N-terminus may also be acetylated.

Additionally, peptide NQHTPR (SV6D; SEQ ID NO:5) was designed to bind to strategic receptors that are regulated by glycans containing terminal N-acetylgalactosamine or galactose. SV6D (SEQ ID NO:5) strongly stimulated proliferation and activation of immune cells in the peritoneal cavity and effectively inhibited progression of ascites in a model of ovarian cancer. It is expected that this peptide is also effective in treating cancers of other peritoneal organs. The active sequences of the relevant peptides were described previously [U.S. Pat. Nos. 7,838,497 and 8,460,697, incorporated by reference thereto].

In a preferred embodiment, the peptides of the invention comprise a peptide construct with at least two arms. The construct typically has a central framework and each arm comprises a therapeutic sequence linked to the central framework via a linker. Each therapeutic sequence of the peptide construct can be the same or different. In a preferred embodiment, the therapeutic sequence is the same for each arm of peptide construct. The therapeutic sequence is preferably selected from the group of therapeutic peptides described above. The present invention also provides therapeutic compositions comprising at least one peptide of the invention and a pharmaceutically acceptable carrier. In a preferred embodiment, the composition is an immunostimulatory composition, preferably further comprising an antigen and/or an antibody preparation admixed therewith in an amount sufficient to enhance antibody-mediated cytotoxicity or phagocytosis. Alternatively, the composition may comprise an immunoglobulin admixed with the therapeutic peptide in an amount sufficient to substantially enhance passive immune protection, e.g., at least 30% increase compared to the control.

In another embodiment, the therapeutic compositions comprises a carrier; at least one agent selected from the group consisting of: a B cell proliferation agent, a dendritic cell proliferation agent, a cytotoxic T cell proliferation agent, or a NK cell proliferation agent; and a therapeutic peptide or a multivalent structured polypeptide as described above. In certain embodiments, the composition further comprises an antibody preparation admixed in an amount sufficient to enhance antibody mediated cellular cytotoxicity in a subject; or further comprises an immunoglobulin admixed with the polypeptide composition in an amount sufficient to enhance passive immunoprotection.

Preferred cytotoxic T cell proliferation agents and/or NK cell proliferation agents include molecules that increase IL-2, IL-15 and IL-21 expression. Alternatively, molecules that induce IL-12 and IL-18 expression are included.

The peptides of the invention are useful in treating the subject having a disease, especially those diseases treatable by endogenous induction of antibodies against invading pathogens or endogenous antigens of harmful cells. The peptides of the invention can specifically be used to treat such diseases as viral infections, cancer, bacterial and yeast infections, and/or other autoimmune diseases, which require treatment through stimulation of the immune system. Such autoimmune diseases include rheumatoid arthritis, psoriasis; dermatitis; systemic scleroderma and sclerosis; responses associated with inflammatory bowel disease; Crohn's disease; ulcerative colitis; respiratory distress syndrome; adult respiratory distress syndrome (ARDS); dermatitis; meningitis; encephalitis; uveitis; colitis; glomerulonephritis; allergic conditions; eczema; asthma; conditions involving infiltration of T cells and chronic inflammatory responses; atherosclerosis; leukocyte adhesion deficiency; systemic lupus erythematosus (SLE); diabetes mellitus; multiple sclerosis; Reynaud's syndrome; autoimmune thyroiditis; allergic encephalomyelitis; Sjorgen's syndrome; juvenile onset diabetes; immune responses associated with acute and delayed hypersensitivity mediated by cytokines and T lymphocytes; tuberculosis; sarcoidosis; polymyositis; granulomatosis; vasculitis; pernicious anemia (Addison's disease); diseases involving leukocyte diapedesis; central nervous system (CNS) inflammatory disorder; multiple organ injury syndrome; hemolytic anemia; myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; idiopathic thrombocytopenic purpura (ITP) and autoimmune thrombocytopenia.

The invention encompasses methods of substantially activating subsets of lymphocytes in a subject, in particular NK cells that attack diseased cells directly or by antibody-dependent cellular cytotoxicity, which complements activation of Fc-mediated phagocytosis, to treat a subject. In a preferred embodiment, HIV-1 replication is inhibited in the subject by at least 50%, more preferably by at least 90% as compared to a control and/or levels prior to administration of the peptide in the subject. In the presence of antibodies, inhibition may reach 100%.

In a preferred embodiment, to provide a non-specific therapeutic agent with a relatively broad front, an agent that activates DCs, B cells, T cells, NK and cytotoxic T cells preferably works in concert with the phagocytic cells of the immune system. The peptides of the present invention can accomplish this goal by concomitantly stimulating the immune cells, including NK cells and phagocytes, and to respond in particular to the presence of pathogen-directed antibodies. Treatment with the peptides of the present invention therefore preferably induce activation of cells of the immune system in vivo and provide a sustained endogenous defense against the pathogen.

In the following description, and for the purposes of explanation, numerous specific details are set forth in order to provide a thorough understanding of the various aspects of the invention. It will be understood, however, by those skilled in the art, that the structures, compositions, and methods are sometimes shown or discussed generally in order to avoid obscuring the invention. In many cases, a description of the material and operation is sufficient to enable one to implement the various forms of the invention. It should be noted that there are many different and alternative technologies and treatments to which the disclosed inventions may be applied, and the full scope of the inventions is not limited to the examples that are described below. Unless otherwise defined, all technical and scientific terms used herein have the same meaning as commonly understood by one of ordinary skill in the art to which this invention belongs.

The term "pharmaceutically acceptable" as used herein means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Preferably, the subject being treated by the methods described herein is a mammal, e.g., monkey, dog, cat, horse, cow, sheep, pig, and more preferably the subject is human.

"Effective amount" or "therapeutically effective amount" is meant to describe an amount of therapeutic peptide or composition of the present invention effective to modulate the innate and adaptive immune systems and/or treat or prevent a disease in a subject and thus produce the desired therapeutic effect in the subject.

Typical compositions and dosage forms may comprise one or more excipients. Suitable excipients are well known to those skilled in the art of pharmacy, and non-limiting examples of suitable excipients are provided herein. See, e.g., Remington's Pharmaceutical Sciences, 18th ed., Mack Publishing, Easton Pa. (1990).

The present invention comprises therapeutic peptides, compositions of those therapeutic peptides for administration to a subject in need, and methods to stimulate the immune system of a subject through the administration of compositions containing those therapeutic peptides. In general, the advantage of this invention is the modulated release of specific cytokines and the stimulation of immune cells, including but not limited to B cells, NK cells, $CD8^+$ T cells and phagocytes, to respond to the presence of pathogen-directed antibodies. Non-limiting examples of cytokines include immunoregulatory proteins such as interleukins and interferons, which are secreted by cells of the immune system and can affect the immune response. A non-limiting example of the stimulation of immune cells is the induction of Fc-mediated phagocytosis. An additional example is direct activation of NK cells for antibody-dependent cellular cytotoxicity. A further example is activation of NK cells and CTL to lyse infected or cancer cells by direct cellular cytotoxicity.

The single letter designation for amino acids is used predominately herein. As is well known by one of skill in the art, the single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; Y is tyrosine.

The therapeutic peptide is preferably 5 to 8 amino acids. Preferred therapeutic peptides are selected from the group consisting of:
VGGGS (SEQ ID NO:1) and $X1-X2-X3-X4-X5-X6-X7-X8$, wherein:
X1 is selected from the group consisting of H and N;
X2 is selected from the group consisting of P and Q;
X3 is selected from the group consisting of S and H;
X4 is selected from the group consisting of H, T, and L;
X5 is selected from the group consisting of P and K, or is absent;
X6 is selected from the group consisting of R, L and S, or is absent;
X7 is selected from the group consisting of S and L, or is absent; and
X8 is G, or is absent;
In a most preferred embodiment, the therapeutic peptide is selected from the group consisting of: VGGGS (SEQ ID NO:1), HPSLK (SEQ ID NO:2), NPSHPLSG (SEQ ID NO:3), NPSHPSLG (SEQ ID NO:4) and NQHTPR (SEQ ID NO:5).

Multivalent structured polypeptides comprising multiple copies of the therapeutic peptide are preferred. In one embodiment, the multivalent structured polypeptide comprises a construct and at least two arms, the construct having a central framework and each arm comprising a therapeutic peptide sequence linked to the central framework via a linker, wherein each therapeutic sequence is preferably the same.

As used herein, "construct" is defined as the entire molecule and comprises the central framework linked with at least two arms. In a preferred embodiment, the construct comprises the central framework linked to 2 or more arms, e.g., 3, 4, 5, 6, 7, 8, 9, 10, 11, or 12 arms, preferably 2 to 8 arms. In a further preferred embodiment, the construct comprises the central framework linked to 4 arms. Each arm within the construct may consist of the same or different therapeutic sequence and/or linker. In one preferred embodiment, the therapeutic sequence is the same between arms.

The "central framework" provides a structure for attaching the arms. The central framework is based on a core molecule, which has at least two functional groups to which molecular branches having terminal functional groups are bonded, e.g., a tri-lysine to which the peptide arms are added. Such molecules may be developed or created to present a varying number of branches, depending on the number of monomers branched from the core molecule. Each terminal functional group on each branch provides a means of attachment to an arm. Non-limiting examples of preferred central framework include: ethylenediamine (1,2-ethanediamine), ethylene glycol (1,2-dihydroxyethane), polyols such as glycerol, 3,5-diaminobenzoic acid, 1,3,5-triaminobenzene, and monocarboxylic-diamino compounds of intermediate length. Preferably, the monocarboxylic-diamino compounds are within the range of 2 to 10 carbons in length. Non-limiting examples of such compounds are 2,3-diaminopropionic acid and 2,6-diaminocaproic acid. In a more preferred embodiment, the monocarboxylic-diamino compound is 6 carbons in length. Compounds that provide an aromatic central framework which absorbs light may be beneficial for determining peptide concentration as well. The carboxyl group of the monocarboxylic-diamino compounds allows the addition of C-terminal tags including biotin derivatives. In a preferred embodiment, the central framework comprises a tri-lysine core (a lysine residue as the central molecule bonded to two lysine residues, each through its carboxyl group, to one of the amino groups of the central lysine residue), providing a central framework for four arms.

The "arm" comprises the therapeutic sequence, plus the linker. The "linker" comprises a peptide chain or other molecule that connects the central framework to the core sequence. In a preferred embodiment, the linker comprises, but is not limited to, certain linker peptide sequences, polyethylene glycol, 6-aminocaproic acid (6-aminohexanoic acid), 8-aminooctanoic acid, and dextran. In a most preferred embodiment, the linker is GGGS (SEQ ID NO:6), GGGSGGGS (SEQ ID NO:7), SSSS (SEQ ID NO:8), SSSSSSSS (SEQ ID NO:9), or variations thereof. The length of the linker can be adjusted, for example, the linker GGGS (SEQ ID NO:6) can be repeated to provide variable lengths, e.g., repeated twice (GGGSGGGS (SEQ ID NO:7)), or even three or more times; additional serine residues could be added to SSSS (SEQ ID NO:8) to also produce varying lengths of the linker. The therapeutic peptide preferably functionally mimics a terminal sequence 5-acetylneuraminic acid-galactose on complex glycans, the terminal sequence being linked α(2,3) or α(2,6). In some aspects, the therapeutic peptide functionally mimics a terminal sequence 5-acetylneuraminic acid-galactose or N-acetylgalactosamine on complex glycans, the terminal sequence being linked α(2,3) or α(2,6). The therapeutic peptides are advantageously configured to bind to the receptor NKG2D and/or sialic acid-binding immunoglobulin-like lectins and function as modulators of the immune system by binding to receptors on B cells, DCs, NK cells, T cells, cytotoxic T cells and/or phagocytic cells.

The therapeutic peptide is preferably administered in an amount sufficient to induce activation of NK cells in the subject and the subject is a human. In one embodiment, the therapeutic peptide or multivalent structured polypeptide is administered in an amount sufficient to induce antibody-mediated cellular cytotoxicity in the subject, preferably to increase the expression of at least one endogenous cytokine from lymphocytes elected from the group consisting of: IL-2, IL-4, IL-12, IL-16, IL-17, IL-21, TNF-β, IFN-γ and RANTES and/or decreases at least one endogenous cytokines elected from the group consisting of: IL-1α, IL-1β, IL-13, TNF-α.

The method may advantageously further comprise the step of administering an antibody preparation admixed in an amount sufficient to enhance antibody-mediated cellular cytotoxicity.

The step of determining the level of immune cells such as B cells, NK cells and/or CD8$^+$ cytotoxic T cells in the subject's blood is done using well known methods in the art, e.g., flow cytometric analysis of peripheral blood mononuclear cells with use of antibodies against cell-specific surface markers. It is advantageous to further establish a ratio of NK cells and/or CD8+ cytotoxic T cells compared to monocytes in the subject's blood. In a preferred embodiment, the ratio of NK cells or CD8+ cytotoxic T cells to monocytes is 3:1 or more preferably 4:1. The present invention is most effective with a higher ratio NK cells and/or CD8+ cytotoxic T cells compared to monocytes.

The present invention identifies a series of peptides that stimulate immune response and modulate the release of specific cytokines. Thus, in a first aspect, the present invention provides a therapeutic peptide consisting of 9 to 12 amino acids in length (including a spacer sequence). In a preferred embodiment, the therapeutic peptide is in a substantially purified form. As used herein, the term "substantially purified" refers to material that is substantially or essentially free from components which normally accompany it as found in its synthesized state. When the material is synthesized, the material is substantially or essentially free of cellular material, gel materials, culture medium, chemical precursors, contaminating polypeptides, nucleic acids, endotoxin, and other organic chemicals. Preferably, the peptide is purified to represent greater than 90% (peptide content) of all organic molecular species present. More preferably the peptide is purified to greater than 95% (peptide content), and most preferably the peptide is purified to essential homogeneity, wherein other organic molecular species are not detected by conventional techniques. Advantageously, the therapeutic peptide is reacted with acetic anhydride to acetylate the N-terminus of the therapeutic peptide. Acetylation protects the peptide from N-terminal degradation and therefore is preferred.

SCIENTIFIC BASIS OF THE INVENTION

Peptide sequences were identified by computer-aided molecular modeling of docking to the sugar-binding site of plant lectins, which served as receptor analogs. The concept underlying the design of Susavion's peptides had several components. From knowledge that a number of receptors on cells of the immune system bind carbohydrate ligands [20,21], we focused on developing peptidic mimetics of these glycan ligands. Peptides of 5 to 8 amino acids in length fill the glycan binding site of lectins and receptors and are sufficiently short to be invisible to the antigen-presenting processes of the immune system. An important aspect of the final peptide is a multivalent structure that is capable of cross-linking receptors, an event that is critical to initiation of a signal transduction pathway within the cell [30,31]. To determine the most effective amino acid sequence of a peptide, molecular modeling was performed of docking of a single (monovalent) sequence into the glycan-binding site of well-characterized plant lectins, which were selected as analogs of cell-surface receptors. The crystal structures of the lectins were downloaded from the Protein Data Bank (PDB). ArgusLab 4.0.1 software (Mark A. Thompson, Planaria Software LLC, Seattle, Wash.) was used for modeling. Amino acid residues that comprise the binding site of a lectin or receptor were selected from the literature that describes each protein. Through this approach, unique peptide sequences were evaluated by predicted binding energy. These in silico experiments predicted that some peptides would bind to a variety of lectins with sufficiently high affinities to encourage further characterization.

Figure 2:
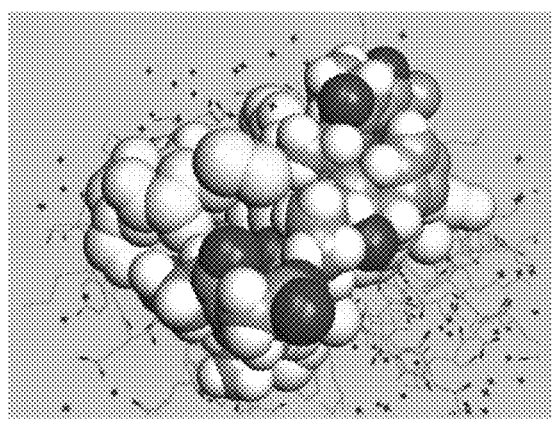

A model for interaction of the peptide designated SVH1C (SEQ ID NO:3) with the glycan-binding site of the lectin-type receptor Siglec-5 (accession no. 2ZG1) is illustrated in FIG. 1. The family of siglec receptors is specific for ligands containing terminal sialic acid (also called 5-acetylneuraminic acid, Neu5Ac). Siglec-5 binds with high specificity to glycans containing a terminal Neu5Ac(α2,8)Neu5Ac and or Neu5Ac(α2,6)Gal linkage. The predicted value for ΔG' of −47 kJ/mol corresponds to a $K_D$ of $1 \times 10^{-8}$ M for the monovalent peptide. Cell-surface receptors that bind to these sugars include the family of siglecs and NKG2D, an important activating receptor on NK cells and CD8$^+$ cytotoxic T cells. Although NKG2D has a variety of peptide/protein ligands in vivo [17,29], the C-type lectin domain of this receptor suggested that it may also bind to glycans. This hypothesis was affirmed when Imaizumi et al. [18] demonstrated that NKG2D binds glycans with specificity for Neu5Ac(α2,3)Gal. The ligand-binding site of NKG2D (accession no. 1MPU) was constructed from data presented by Li et al. [32] and McFarland et al. [33]. Modeling predicted highly favorable binding energy to NKG2D, with a ΔG' of −40 kJ/mol, which corresponds with a $K_D$ of about $1 \times 10^{-7}$ M (FIG. 2).

Figure 3:
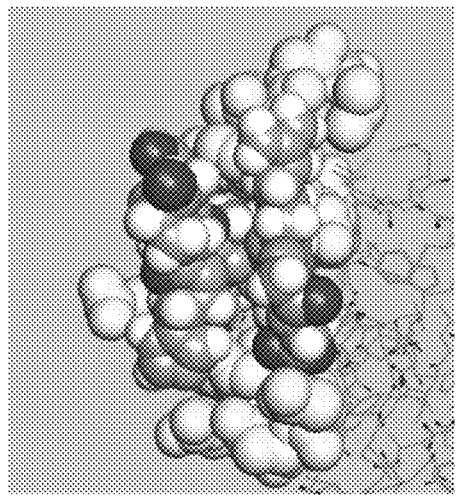

A model for interaction of the peptide designated SV6D (SEQ ID NO:5) with the glycan-binding site of the lectin-type receptor asialylglycoprotein receptor-1 (ASGPR-1) (accession no. 1DV8) is illustrated in FIG. 3. ASGPR-1 is a homolog of CLEC10a and has a strong preference for binding N-acetylgalactosamine over galactose [34]. The predicted value for ΔG' of −40 kJ/mol corresponds to a $K_D$ of $1 \times 10^{-7}$ M for the monovalent peptide.

Figure 4:
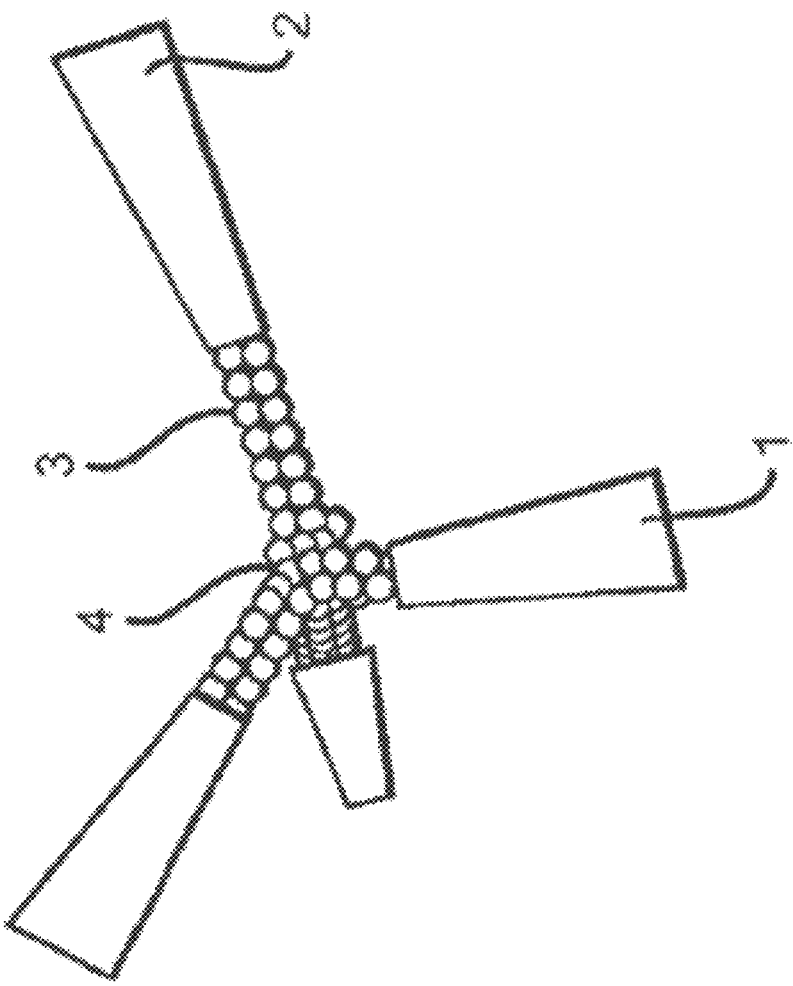
Figure 5:
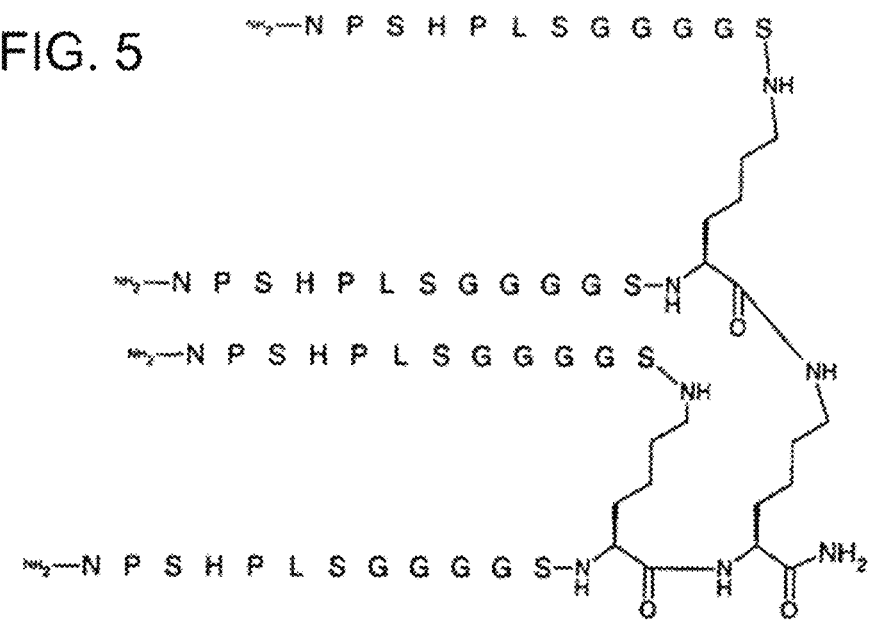
Figure 6:
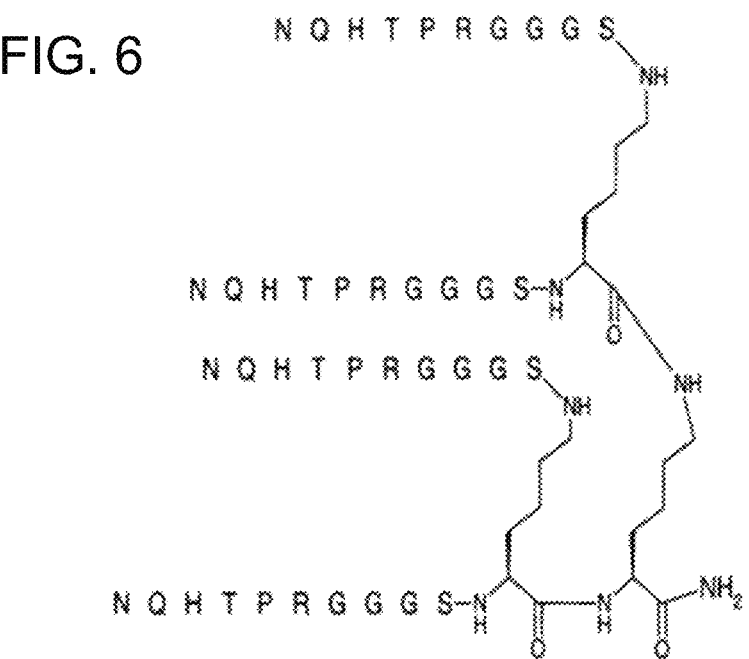

The short peptide sequence was then incorporated into multivalent structures (FIG. 4). This design was based on the concept of avidity as a function of ligand density and entropic factors. The theoretical basis for multivalency was provided by Mammen et al. [35], Dimick et al. [36] and Cairo et al. [37]. Multivalency should provide much more favorable binding energy than predicted by molecular modeling. Although monovalent peptides should be active, multivalency of ligands provides high avidity interactions and facilitates cross-linking of receptors, which is often required for activation of cellular responses [30,31]. FIG. 5 illustrates the final quadravalent structure with the active sequence NPSHPLSG (SEQ ID NO:3). FIG. 6 illustrates the final quadravalent structure with the active sequence NQHTPR (SEQ ID NO:5).

Direct Binding of Peptides to Lectins

The binding of SVH1C to lectins such as MAA and SNA1 [19] suggests that the peptide mimics Neu5Ac-Gal sequences on the termini of complex glycans. This sequence is a ligand for the receptor NKG2D on NK cells and by T cells and CD8+ cytotoxic T cells [18]. Also, a family of 14 lectin-type receptors, the siglecs (sialic acid-binding Ig-like lectins), binds Neu5Ac-Gal- sequences (reviewed in reference 13). The siglecs are thought to promote cell-cell interactions and regulate the functions of cells in the innate and adaptive immune systems through glycan recognition. These receptors are possible targets of the peptide, as predicted by molecular modeling (FIGS. 1-3). Whereas NKG2D is specific for the Neu5Ac($\alpha$2,3)Gal linkage, members of the siglec family express specificity for the $\alpha$(2,3) or $\alpha$(2,6) linkages. Thus the peptides have the flexibility to bind to all of these receptors.

Binding of SVH1C to NKG2D and Siglecs

NKG2D is not known to function as a glycan receptor in vivo, although the Neu5Ac($\alpha$2,3)Gal structure binds to the C-type lectin domain of the receptor (18). On the other hand, the siglecs have been characterized as receptors that bind Neu5Ac($\alpha$2,3)Gal or Neu5Ac($\alpha$2,6)Gal [13-15]. These receptors function as either inhibitory or activating when bound with a ligand. Siglec-1 is expressed on macrophages and is involved in cellular adhesion but also enhances endocytosis [13]. As such, it enhances infection of these cells by HIV-1 by binding to glycans on the envelop of the virus [38-39]. Expression of other siglecs is distributed on other cells of the immune system [13-15].

Figure 7:
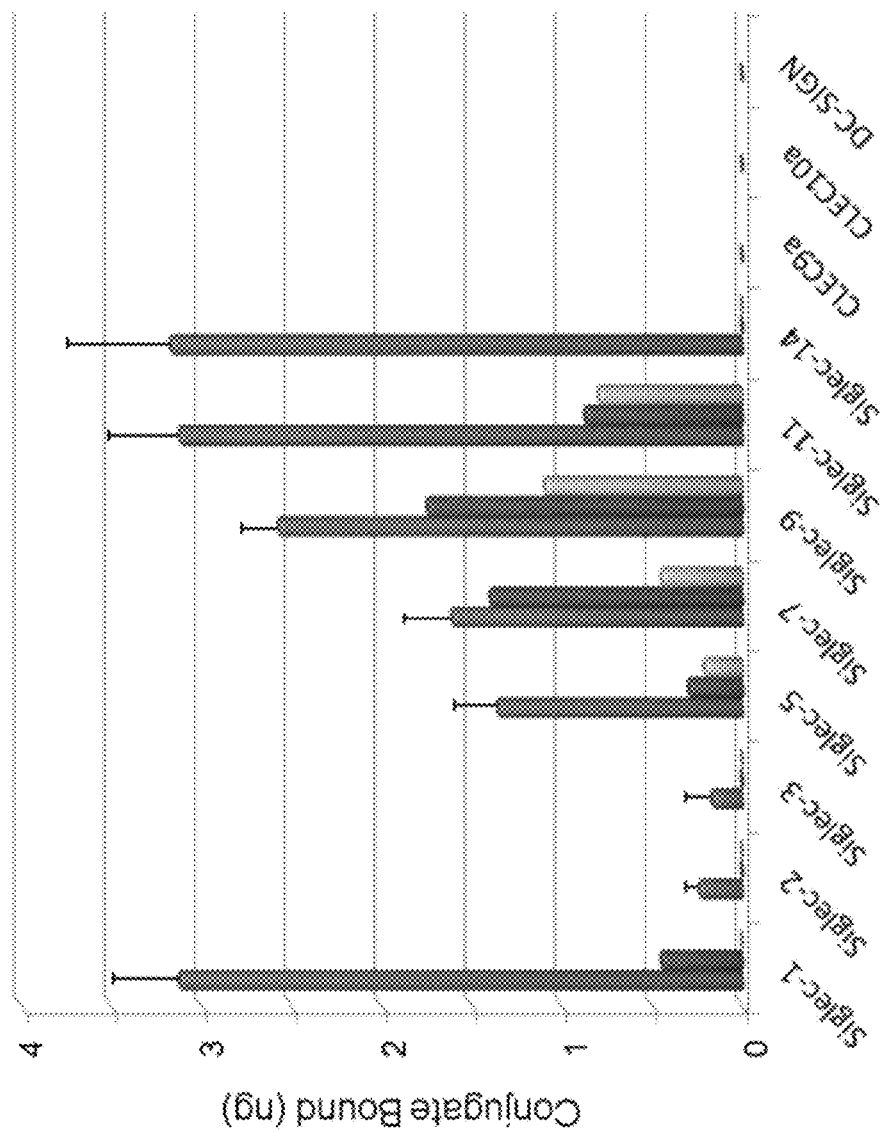
FIG. 7 illustrates the binding of SVH1C (SEQ ID NO:3) to lectin-type receptors, siglecs (sialic acid-binding Ig-like lectin receptors) and other lectin-type receptors in a solid-phase assay. The buffer in these assays was PBS containing 0.05% Tween-20. The Figure shows the amount of streptavidin-peroxidase bound to SVH1C that was bound to the receptors. The receptors were Fc-chimeras and were assayed in protein A/G-coated microtiter wells. Siglec-1 and CLEC10a contained a C-terminal His tag and were assayed in a separate experiment with Ni-coated wells. SEM was determined from four independent experiments run in duplicate. Inhibition by fetuin is shown by the average of two assays in which the glycoprotein was added at 10 µM (second, black bar) or 30 µM (third, light grey bar) in each receptor group. Binding was measured by a colorimetric assay of peroxidase.

Direct binding of SVH1C to siglecs was demonstrated by a solid-phase assay in which recombinant chimeric siglecs were bound in microtiter wells coated with protein A/G. The chimeric siglecs contained an N-terminal glycan-binding domain and a C-terminal Fc$\gamma$ domain, which bound strongly to protein A. Biotinylated peptides were then incubated with the siglecs, the wells were stringently washed and the bound peptide was detected by binding of streptavidin conjugated with peroxidase. FIG. 7 shows results of this assay with several siglecs and additional lectin-type receptors. SVH1C bound strongly to several siglecs but not to CLEC9a, CLEC10a or DC-SIGN. Binding of SVH1C was inhibited by the sialylated protein, fetuin, which indicated that SVH1C likely binds at the glycan-binding site of siglecs. In other experiments, a proteomic analysis of proteins fished from PBMCs with biotinylated SVH1C and streptavidin-agarose identified Siglec-15, an activating receptor found on myeloid cells (40), among the complex of proteins that bound to the peptide. Among myeloid cells that express Siglec-15 are macrophages and dendritic cells [13].

Figure 8:
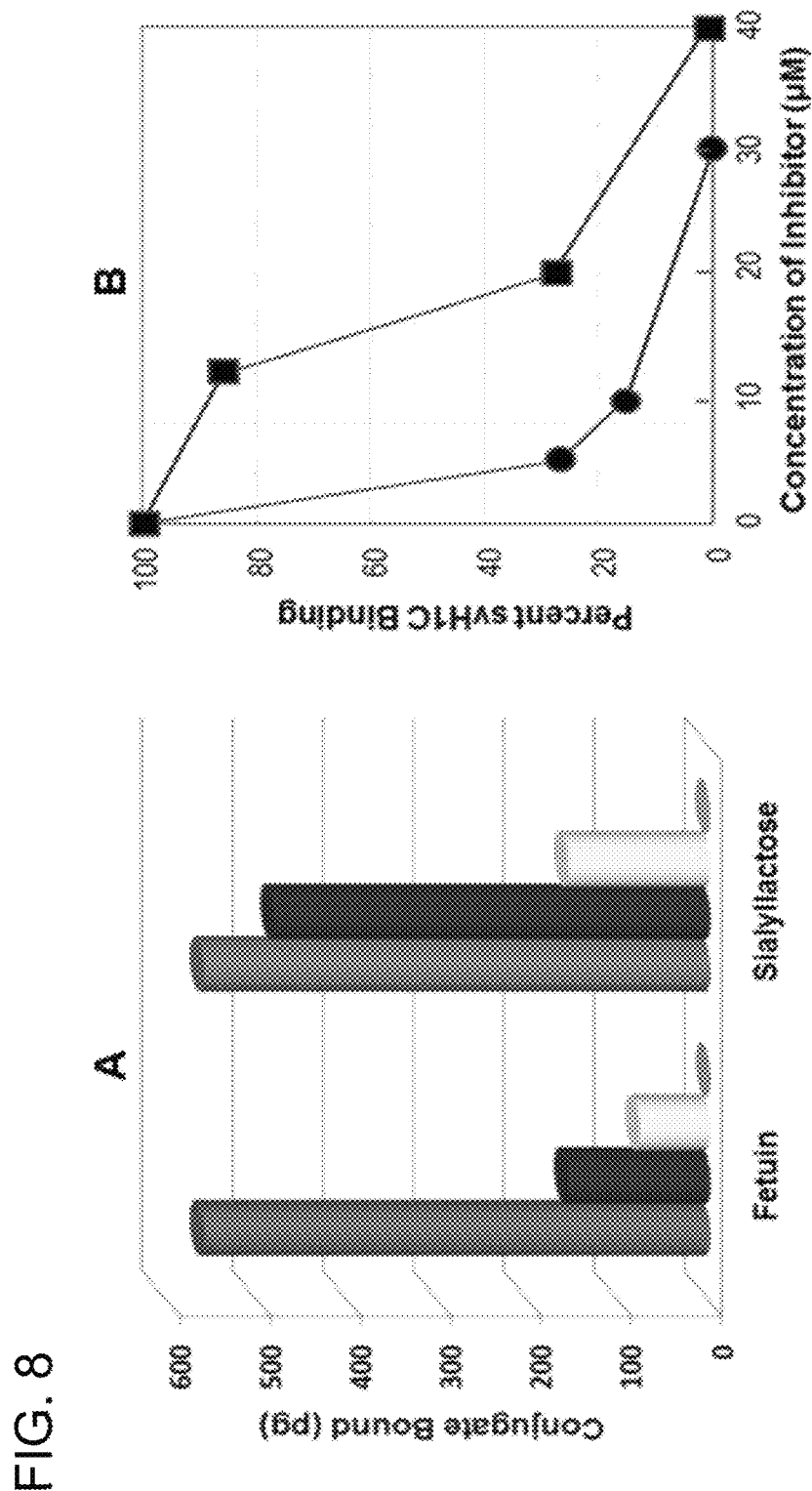
FIG. 8 illustrates the binding of SVH1C (SEQ ID NO:3) to receptor NKG2D in a solid-phase assay. 8A, The amount of streptavidin-peroxidase bound to SVH1C that was bound to the receptor was measured after extensive washing with PBS containing 0.05% Tween-20. Fetuin (5 µM, black bar; 10 µM, light grey bar; 30 µM, grey bar) and sialyllactose (12 µM, black bar; 20 µM, light grey bar; 40 µM, grey bar) were included as inhibitors. Binding was measured by a colorimetric assay of peroxidase. This assay was performed three times. 8B, Graphical representation of inhibition of binding of SVH1C to NKG2D by fetuin (circles) or sialyllactose (squares).

The solid-phase assay was also used to determine binding of SVH1C to NKG2D (FIG. 8). Fc-chimeric NKG2D was bound in microtiter wells coated with protein A/G, which binds strongly to the Fc domain. Binding of biotinylated svH1C was measured by activity of peroxidase conjugated to streptavidin. Strong binding was observed, with a KD of approximately 1 $\mu$M. As shown in FIG. 8, binding of the peptide was inhibited by the fetuin and the trisaccharide sialyllactose, which indicated that the peptide bound in the glycan-binding site on the receptor. The glycoprotein fetuin is an effective probe to confirm binding of the peptide in the glycan-binding site of the receptors. Each molecule of fetuin contains collectively 12 to 15 oligosaccharides that terminate predominantly as Neu5Ac-Gal, with nearly equal $\alpha$(2,3) and $\alpha$(2,6) linkages, on three N-linked and three O-linked glycans [41,42].

Figure 9:
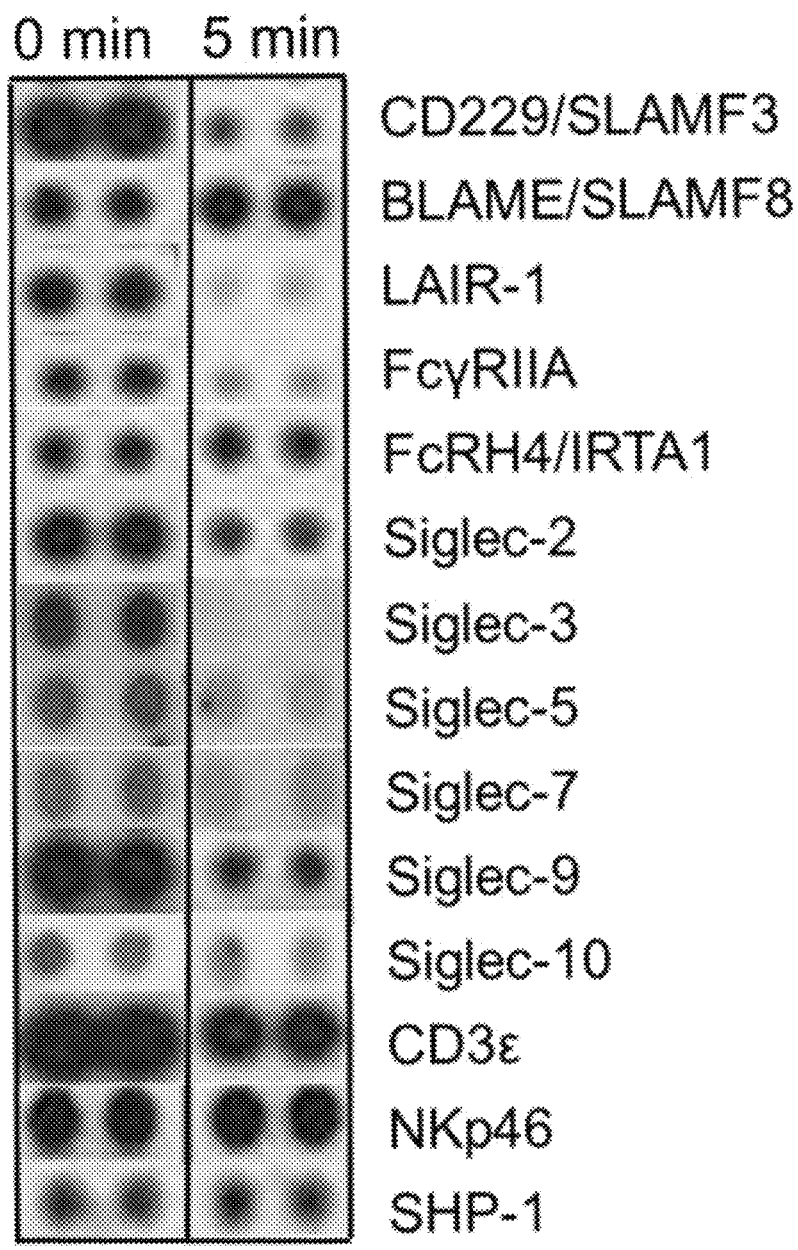
FIG. 9 illustrates the changes in phosphorylation of cell-surface immunoreceptor after treatment of human PBMCs with 100 nM SVH1C (SEQ ID NO:3) for 5 min. Cell lysates were spread on an array of capture antibodies and phosphorylated forms were detected by a phospho-tyrosine antibody (Human Phospho-Immunoreceptor Array, R&D Systems, Minneapolis, Minn.). The phosphorylated forms of CD229, FcγRIIA, LAIR-1, Siglec-2, -3, -5, -7, -9, and -10 decreased, while BLAME (B Lymphocyte Activator Macrophage Expressed) increased. FcRH4, SHP-1 and NKp46 did not change significantly. This experiment showed that the peptide has dramatic effects on human cells.

Among the siglec receptors, most are inhibitory receptors and contain an ITIM (immunoreceptor tyrosine-based inhibitory motif) within their cytosolic domain, whereas a few, in particular Siglec-14, Siglec-15, and Siglec-16 function with a cytoplasmic activating adaptor protein, DAP12 [13,40]. NKG2D is also an activating receptor and functions in association with the cytoplasmic, adaptor proteins DAP10 and DAP12, which contain an ITAM (immunoreceptor tyrosine-based activation motif) [17,29]. The function of these receptors is regulated by phosphorylation of the tyrosine residue within the regulatory motif. As illustrated in FIG. 9, treatment of human peripheral blood mononuclear cells (PBMCs) with 100 nM SVH1C for 5 min caused dramatic changes in the phosphorylation state of several receptors. Phosphorylated inhibitory receptors commonly function by recruiting SHP-1, a phosphatase that inactivates other receptors [13-15]. Thus, dephosphorylation of these receptors attenuates their activity.

In Vivo Proliferation of Immune Cells

Figure 10:
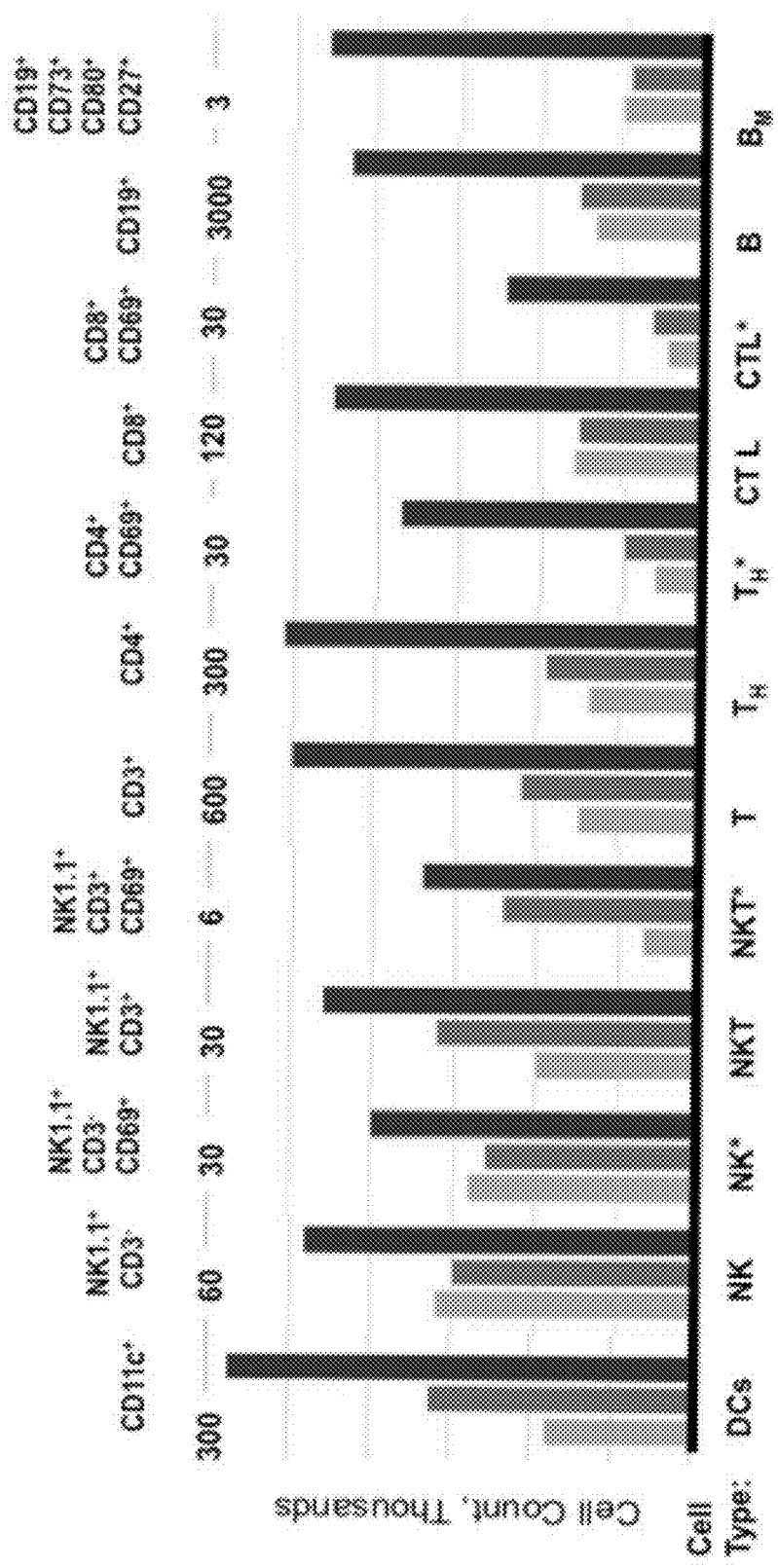
FIG. 10 illustrates that alternate-day subcutaneous injection of SVH1C (SEQ ID NO:3) into C57BL/6 mice resulted in relatively large increases in populations of immune cells in the peritoneal cavity. The bars, in increasing darkness, show populations of specific cell types at 1, 3 and 5 days of treatment, i.e., 24 hours after each injection at day 0, 2 and 4. Peritoneal cells were obtained from 3 animals, pooled, and analyzed by flow cytometry. The markers used to identify cell types are listed across the top of the figure. The total number of each cell type is plotted, with the scale indicated at the top of each cell type. Cells are identified by the usual designations across the bottom of the figure. An asterisk indicates the activated populations that express CD69.

To determine whether a decrease in activity of inhibitory receptors is reflected by stimulation of proliferation of immune cells in vivo, SVH1C (SEQ ID NO:3) was injected subcutaneously every other day at a dose of 1 nanomole per gram body weight and populations of immune cells in the peritoneal cavity were measured by flow cytometry. Injections were administered on day 0, 2 and 4, and peritoneal lavage was performed to obtain immune cells. Cells from three animals at each time point were pooled and analyzed by flow cytometry. As illustrated in FIG. 10, most cells types proliferated over the period of treatment. In particular, DCs (CD11c+), NK cells (NK1.1+), CD3+, CD4+ and CD8+ T cells, and B cells (CD19+) populations increased several-fold, including those that expressed the activation marker CD69+. In particular, memory B cells, which express CD73, CD80 and CD273, increased significantly. The number of immune cells increased by at least 1.5 fold, at least 2 folds, at least 2.5 folds, at least 3 folds, at least 3.5 folds, at least 4 folds, at least 4.5 folds, or at least 5 folds with the administration of SVH1C (SEQ ID NO:3) compared to the number of immune cells prior to the treatment.

Figure 11:
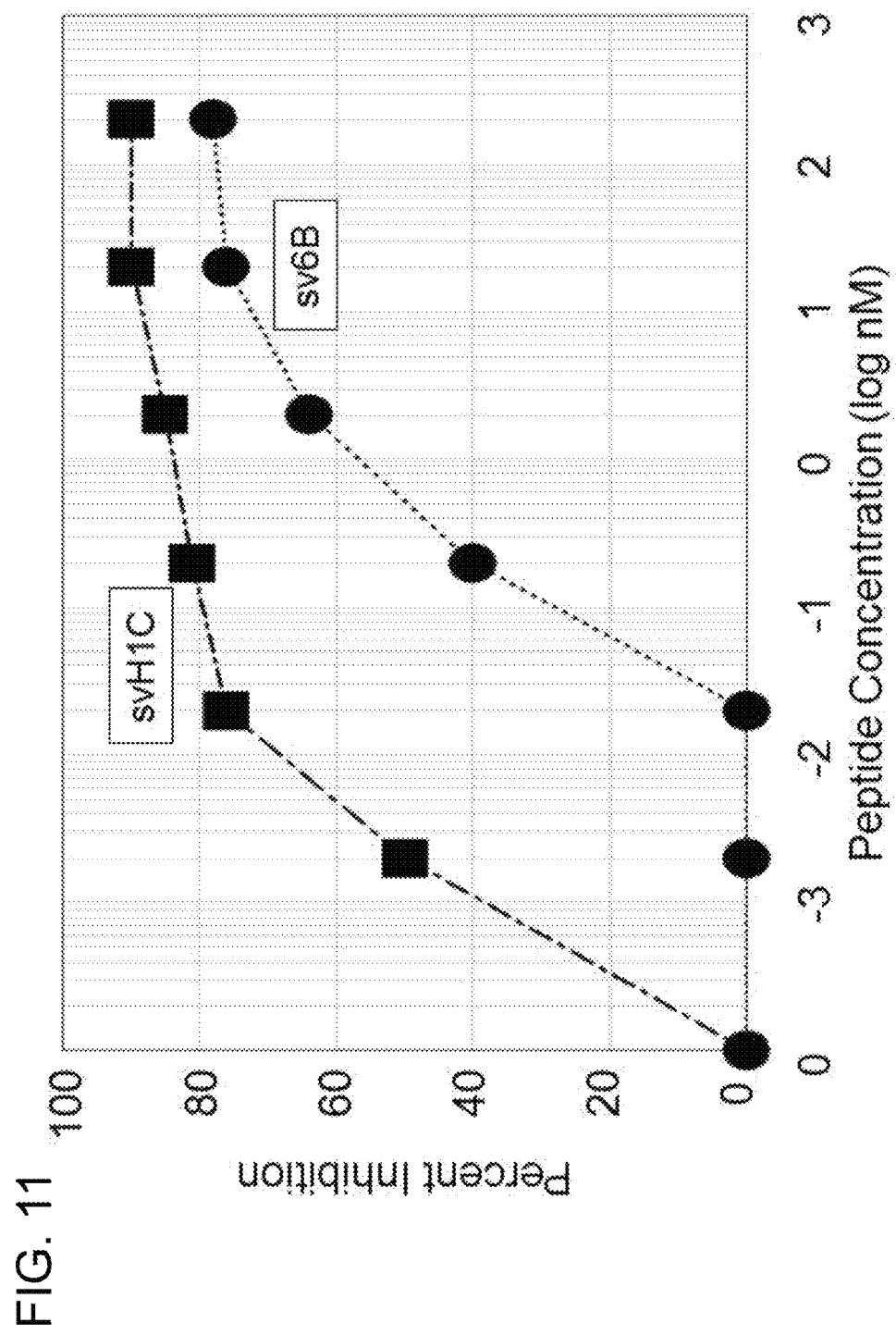
FIGS. 11A-11B show the antiviral activity of SVH1C (SEQ ID NO:3) and SV6B (SEQ ID NO:2) by inhibition of HIV-1 replication in PBMC cultures without anti-HIV antibodies.

In a test of the activity of SVH1C to inhibit replication of viral replication, an experiment was conducted with PBMCs in which SV6B (SEQ ID NO:2) and SVH1C (SEQ ID NO:3) were added to cultures to which HIV-1 was added at a low titer. It was found that when the cultures were overwhelmed with a high input of the virus, the percent of neutralization was reduced. Thus, in subsequent experiments the viral input was reduced to about 30 TCID50. An assay was performed in which peptides were added to the culture without antiserum. For the results shown in FIG. 11, the peptides alone inhibited viral replication by 80 to 90%. IC50 values in this experiment were 2 $\mu$M for SVH1C and about 300 $\mu$M for SV6B. Because antibodies were not present in this experiment, antibody-mediated phagocytosis did not contribute significantly to neutralization. Flow cytometric analysis of the PBMCs indicated a relatively high NK/monocyte ratio in these cultures.

Induction of Cytokine Release

To determine whether activation of cells by the peptides could be detected by induction of release of cytokines, cultured peripheral blood mononuclear cells (PBMCs) were treated with one peptide embodiment of the present invention and, after 4 h incubation, the medium was collected and assayed for changes in the amounts of 40 different cytokines. A therapeutic peptide construct containing four copies of the core sequence VGGGS (SEQ ID NO:1), HPSLK (SEQ ID NO:2) or NSPHPLSG (SEQ ID NO:3) was added at a concentration of 100 nM in each of the assays. Approximately 3 million cells of frozen human PBMCs were thawed at 37° C. and transferred to a 50 mL conical tube where 8 mL of wash medium were added slowly. Then an additional 8 ml of wash medium were added and swirled to mix. The cells were then centrifuged at 330 g for 10 min, the supernatant was removed and the pellet was resuspended in 10 mL wash medium and centrifuged as above. The washed cells were then resuspended in RPMI-1640 medium containing 10% FBS to about 6 million cells per mL and 100 mL of the suspension were added into each well of a 96-well microtiter plate and incubated overnight at 37° C. in humidified 5% $CO_2$. After 24 h the medium was replaced with 200 μL fresh RPMI-1640 medium containing 10% FBS and incubated at 37° C. in humidified 5% $CO_2$ for 2 days. The peptide aliquot was then added to samples in duplicate at a final concentration of 100 nM and incubated at 37° C. in humidified 5% $CO_2$ for 4 h. The medium was then removed and stored at −80° C. The samples were analyzed for production of cytokines. One set of control cells was not treated with an experimental agent. A second set of control cells was treated with lipopolysaccharide, an agent commonly used to induce production of a variety of inflammatory cytokines. The positive control for inflammation was essential to ensure that the peptides did not produce an unregulated inflammatory response.

Culture medium was removed for assay of cytokine levels with methods developed by RayBiotech, Inc. (Norcross, Ga.). In this technology, membrane arrays of antibodies against cytokines are incubated with samples of media. After washing, the array was incubated with a cocktail of all antibodies tagged with biotin. The membrane was then washed free of unbound antibodies and incubated with streptavidin, labeled with a fluorescent dye, which binds to biotin. After a final wash, the membrane arrays were read in a fluorescence detector.

The peptides stimulated release of several important cytokines. In particular, IL-21, a cytokine produced by CD4+ T cells that is required for proliferation and differentiation of natural killer cells and CD8+ cytotoxic lymphocytes. Additional cytokines released by the general population of T cells in response to treatment with the peptides of this invention were IFN-γ, IL-4, IL-8, IL-16, IL-17, TNF-β, and RANTES. Of importance, release of the inflammatory cytokines IL-1α, IL-1β, IL-6, IL-10, and TNF-α were not induced. Release of other important cytokines, notably Eotaxin-2, IL-10, and IL-13, was reduced (Table 1).

TABLE 1

Release of cytokines by PBMC cultures.

| Cytokine | Source | Activity |
|---|---|---|
| *Increased* | | |
| IL-8 | Macrophages | Activation of neutrophils |
| IL-16 | T cells | Lymphocyte chemoattractant |
| IL-17 | T cells | Stimulates secretion of IL-6, IL-8, G-CSF |
| IL-21 | T cells | Mediates innate and adaptive immune responses, affects all lymphocytes, dendritic cells and monocytes |
| IFN-γ | NK cells | Anti-viral, immunoregulatory, anti-tumor properties |
| TNF-β | T cells | Cytolytic or cytostatic for many tumors |
| MIP-1d | T, B, NK cells | Macrophage inflammatory protein, activates dendritic cells, granulocytes, induces synthesis of pro-inflammatory monocytes cytokines |
| RANTES | T cells | Chemotactic for T cells, eosinophils and basophils |
| *Decreased* | | |
| Eotaxin-2 | Dendritic cells, monocytes | Chemotaxis of eosinophils, basophils (inflammatory) |
| IL-10 | Monocytes, macrophages | Inhibits synthesis of IFN-γ, IL-2 and TNF-β |
| IL-13 | T cells | Downregulates inflammatory cytokines |

The mixture of cytokines released from PBMCs, in particular T cells, in response to the peptides described herein should provide, either in isolation or in combination with other treatments, an effective modulation of the immune system. Treatment with the peptides of the present invention should induce activation of cells of the immune system in vivo and provide a sustained endogenous elevation of beneficial cytokines, in contrast to the rapid disappearance of these proteins when given exogenously. These cytokine responses are presumably in addition to direct activation of the immune cells engaged in fighting a disease.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. Although the examples herein disclose the therapeutic efficacy of the peptides of the present invention, with respect to neutralizing replication of the HIV virus, for example, the peptides should be useful to treat a wide variety of infections or disorders, including prophylactic treatments for prevention of such maladies, and for enhancing or stabilizing the well-being of healthy subjects.

Figure 12:
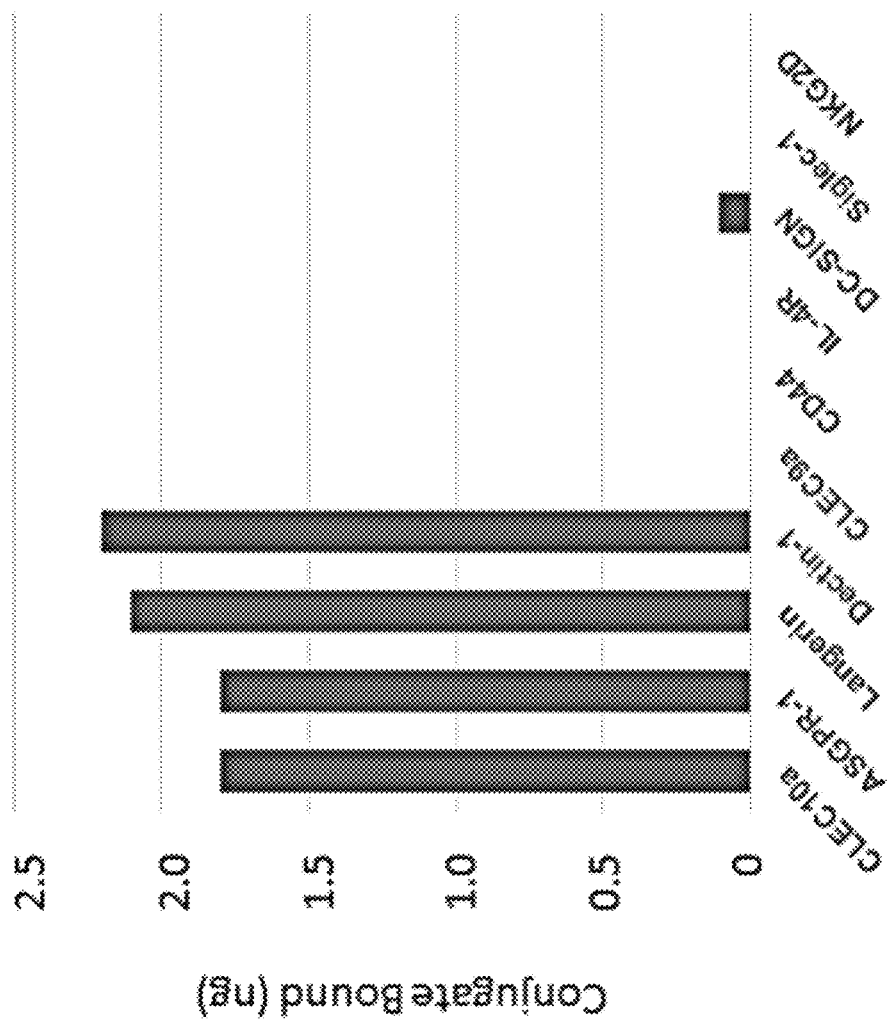
FIG. 12 illustrates the binding of SV6D (SEQ ID NO:5) to lectin-type receptors, CLEC10a, langerin, ASGPR-1, dectin-1, and other lectin-type receptors in a solid phase assay. The buffer in these assays was PBS containing 0.05% Tween-20. The Figure shows the amount of streptavidin-peroxidase bound to SV6D that was bound to the receptors. The receptors were Fc-chimeras and were assayed in protein A/G-coated microtiter wells. The assay was similar to that described under FIG. 7.

Similar experiments were performed to show that SV6D (SEQ ID NO:5) also binds to lectin-type receptors but to a different set as compared with SVH1C (SEQ ID NO:3). Direct binding of SV6D to receptors specific for N-acetyl-galactosamine or galactose was demonstrated by a solid-phase assay in which recombinant receptors containing a poly-histidine tag were bound in microtiter wells coated with Nickel. Biotinylated peptides were then incubated with the receptors, the wells were stringently washed and the bound peptide was detected by binding of streptavidin conjugated with peroxidase. FIG. 12 shows results of this assay with several lectin-type receptors. SV6D bound strongly to CLEC10a, langerin, ASGPR-1 and dectin-1 but not to CLEC9a, DC-SIGN or Siglec-1.

Figure 13A:
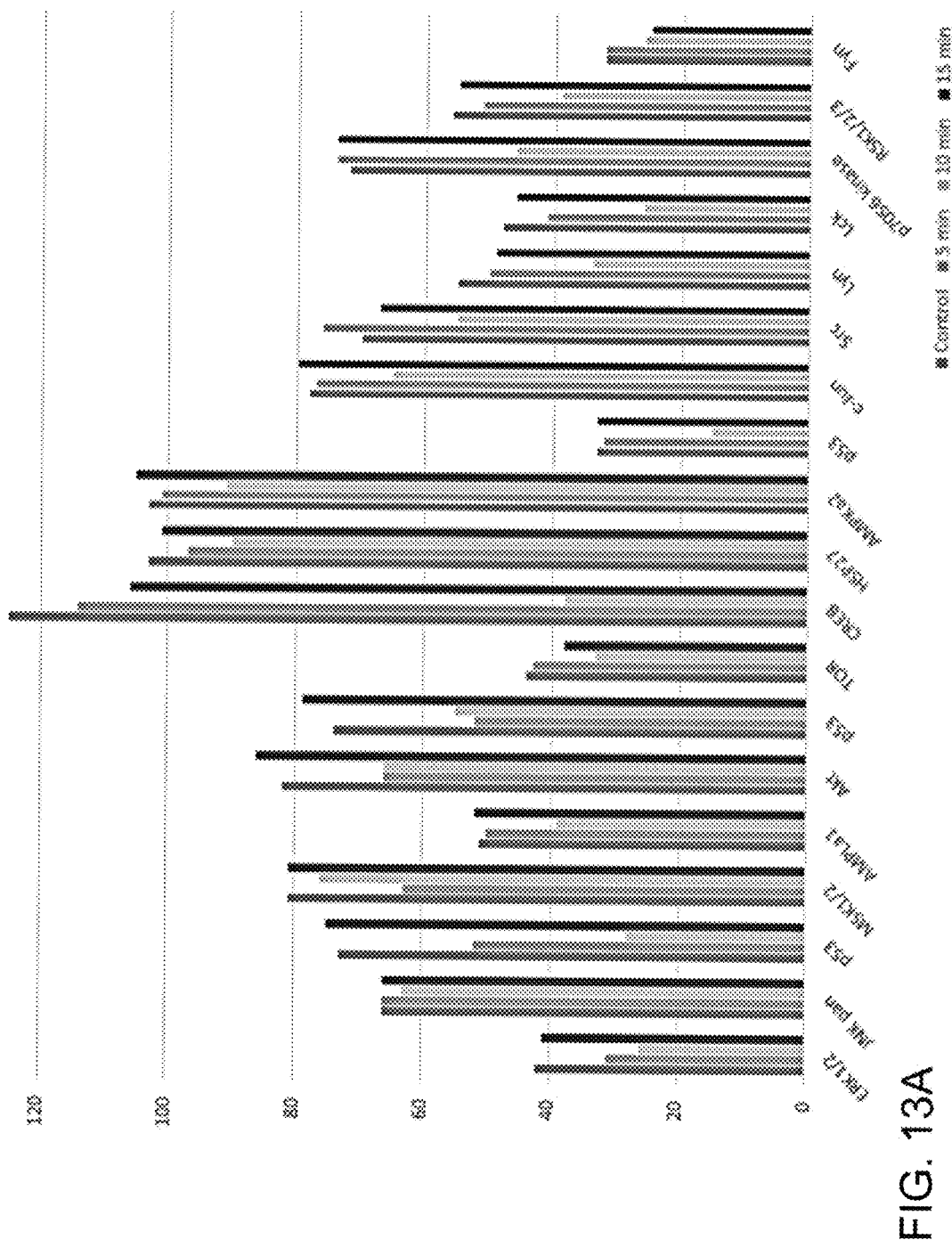
FIG. 13A and FIG. 13B illustrates the changes in phosphorylation of signal transduction kinases in human PBMCs in culture treated with 100 nM SV6D for 5, 10 or 15 min. Cell lysates were spread on an array of capture antibodies and phosphorylated forms were detected with a Human Phospho-Kinase Array (R&D Systems (Minneapolis, Minn.).
Figure 13B:
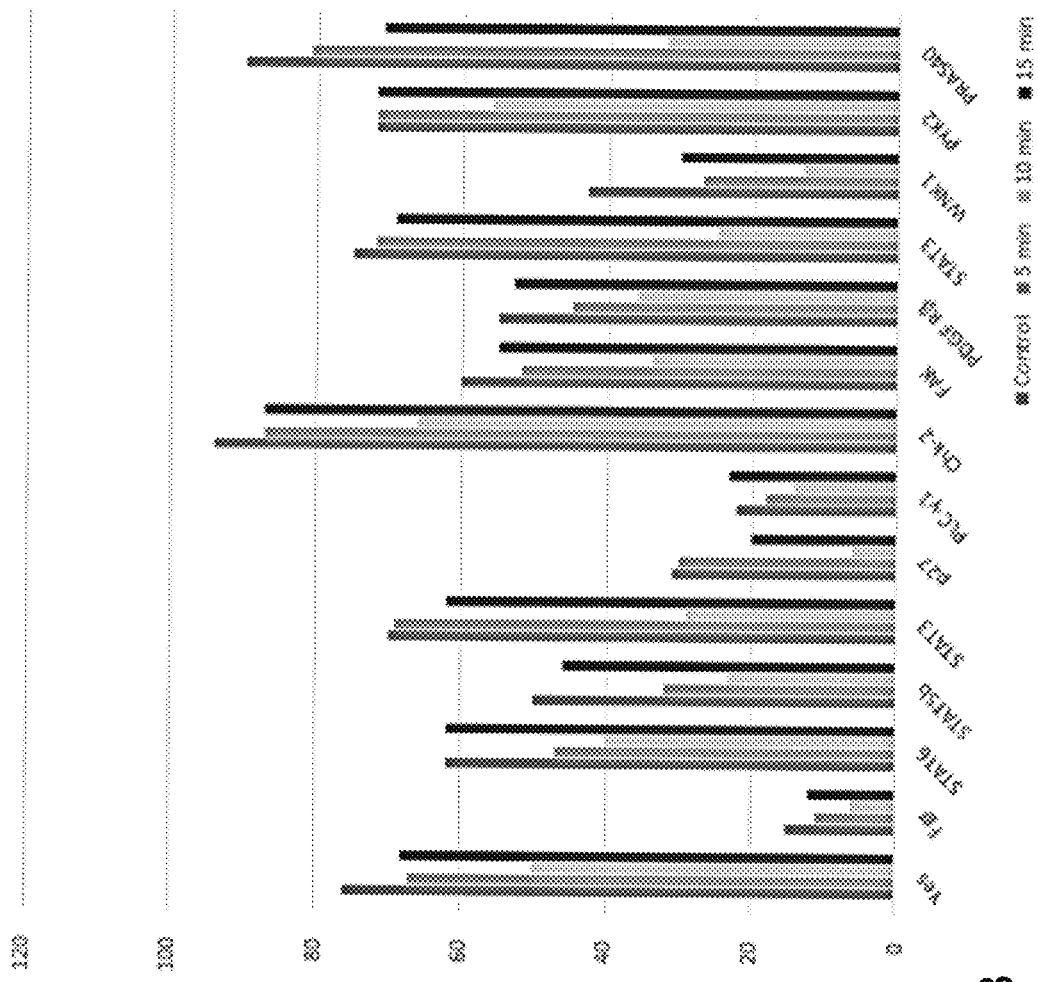

To determine whether binding of SV6D to cell-surface receptors would transfer signals to the cytoplasm of cells, cultures of PBMCs were incubated with 100 nM SV6D and samples were removed after 5, 10 or 15 minutes and compared with the phosphorylation state of signal transduction kinase intermediates in untreated cells. As illustrated in FIGS. 13A and 13B, the phosphorylated form of several intermediates changed rapidly and dramatically. In particular, the phosphorylated forms of proteins p53, CREB and PRAS40 were markedly decreased at 10 minutes but rebounded by 15 minutes. These rapid changes may represent remodeling of the phosphor-proteins.

Figure 14:
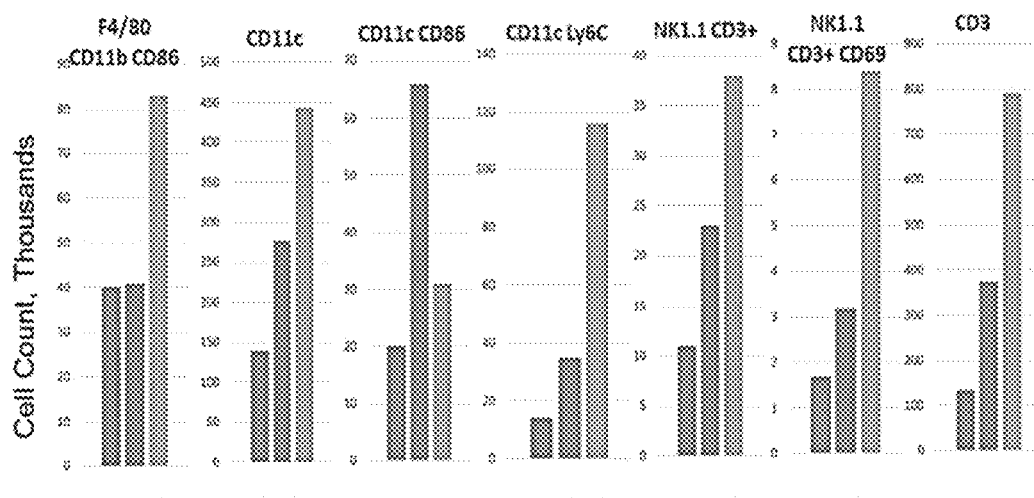
FIG. 14 illustrates that alternate-day subcutaneous injection of SV6D (SEQ ID NO:5) into C57BL/6 mice resulted in relatively large increases in populations of immune cells in the peritoneal cavity. The bars, in increasing darkness, show populations of specific cell types at 1, 3 and 5 days of treatment, i.e., 24 hours after each injection at day 0, 2 and 4. Peritoneal cells were obtained from 3 animals, pooled, and analyzed by flow cytometry. The markers used to identify cell types are listed across the top of the figure. The total number of each cell type is plotted, with the scale indicated at the top of each cell type. Cells are identified by the usual designations across the bottom of the figure. An asterisk indicates the activated populations that express CD69.
Figure 14:
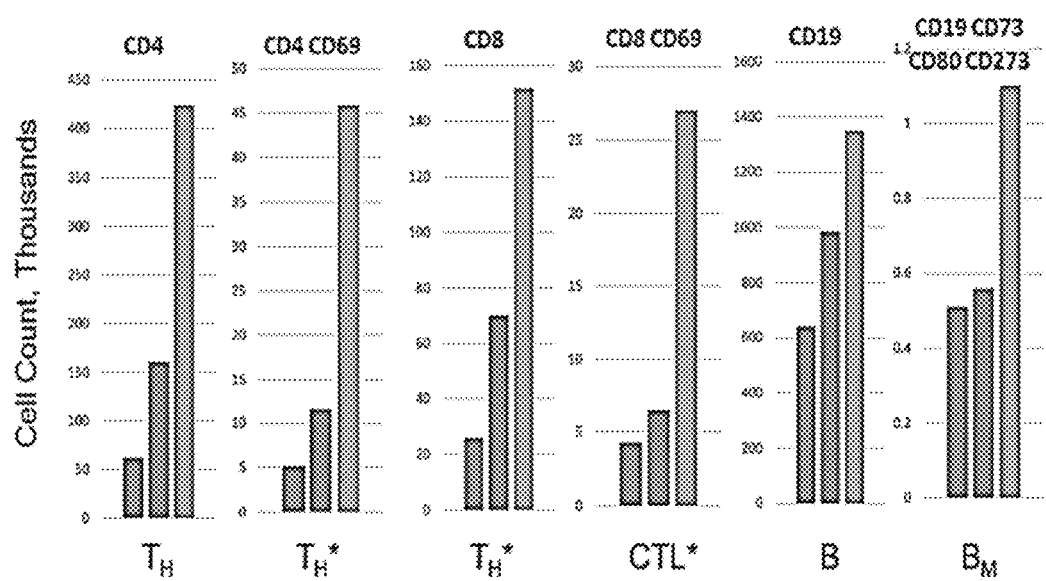

In other experiments, the activity of SV6D (SEQ ID NO:5) to stimulate proliferation of immune cells in vivo was determined. SV6D was injected subcutaneously every other day at a dose of 1 nanomole per gram body weight and populations of immune cells in the peritoneal cavity were measured by flow cytometry. Injections were administered on day 0, 2 and 4, and peritoneal lavage was performed to obtain immune cells. Cells from three animals at each time point were pooled and analyzed by flow cytometry. As illustrated in FIG. 14, most cells types proliferated over the period of treatment. In particular, DCs (CD11c$^+$), NK cells (NK1.1$^+$), CD3$^+$, CD4$^+$ and CD8$^+$ T cells, and B cells (CD19$^+$) populations increased several-fold, including those that expressed the activation marker CD69$^+$.

Figure 15:
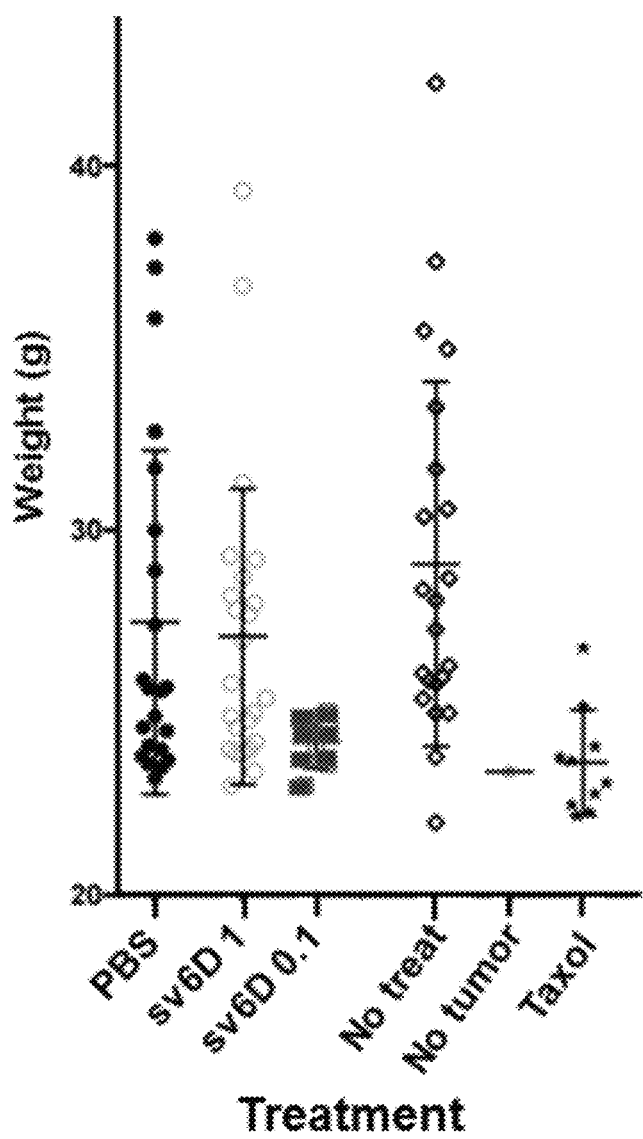
FIG. 15 illustrates the effect of treatment of C57BL/6 mice implanted with an ovarian cancer cell line. Body weights of individual mice were measured during treatment with 1 or 0.1 nmole/g doses of SV6D (SEQ ID NO:5) injected subcutaneously every other day. Ascites formation was evident at the start of treatment and the weights shown are after two weeks of treatment. The effectiveness of the 0.1 nmole/g dose was similar to that of the drug paclitaxel, the currently used chemotherapeutic drug.

A particularly difficult to treat cancer in women is ovarian cancer. A late-stage condition of ovarian cancer is accumulation of ascites in the peritoneal cavity. In a mouse model of ovarian cancer, a cancer cell line was implanted into the peritoneal cavity. The cells form tumors and in time also release malignant cells into the cavity. The activity of SV6D to treat ovarian cancer was tested by alternate-day injections of 1 and 0.1 nanomole per gram of SV6D. Development of ascites was monitored by an increase in body weight of the animals. Ascites accumulation was evident at the start of treatment and the weights shown in FIG. 15 are after two weeks of treatment. The effectiveness of the 0.1 nmole/g dose was similar to that of the drug paclitaxel, the currently used chemotherapeutic drug.

These experiments showed that SVH1C and SV6D, although expressing very different activities in binding to receptors in vitro, had remarkably similar effects in stimulation of proliferation and activation of peritoneal immune cells in vivo. SVH1C has strong antiviral activity (FIG. 11) and SV6D shows strong potential in inhibiting growth of tumor cells (FIG. 15). Therefore, these peptides approach enhancement of immune system activity from different angles, which makes the combination of these peptides a potentially powerful therapeutic embodiment. In other embodiments, SV6D may be used in combination with other therapeutic peptides with predominate antiviral activity, such as the peptides set having the amino acid sequence VGGGS (SEQ ID NO:1), HPSLK (SEQ ID NO:2), NPSHPSLG (SEQ ID NO:4), HPSLG (SEQ ID NO:10), HPSLL (SEQ ID NO:11), HPSLA (SEQ ID NO:12).

Toxicity of Peptides

Human PBMCs were incubated 3 days with peptides and then assay plates were stained with the soluble tetrazolium-based dye MTS to determine cell viability. The mitochondrial enzymes of metabolically active cells metabolize MTS to yield a colored formazan product. After an incubation period of 4 to 6 h at 37° C., the plates were read spectrophotometrically. Cells treated with peptide SVH1C alone or with diluted anti-HIV antiserum were 100±2% viable at peptide concentrations of 1 nM to 1 µM. In another assay to determine cytotoxicity, cells were doubly stained with acridine orange and ethidium bromide. In this assay, viable cells fluoresce green while dead cells fluoresce red. SVH1C did not exhibit cytotoxicity at a concentration of 1 mM, a concentration $10^6$-fold greater than an effective bioactive concentration of 1 nM [43].

Toxicity of the peptide in vivo was tested by injection of a peptide into animals. In preliminary studies on rats, intravenous injections of peptides that provided 1000-fold greater concentrations than an expected therapeutic dose was well tolerated by the animals and no adverse effects of the peptide were been observed. The peptides can be administered in a number of ways, including without limitation by injection (intravenously, subcutaneously, intramuscularly or intraperitoneally, topically (transmucosally, transbuccally, sublingually, or transdermally) and/or orally (liquid, tablet or capsule).

CONCLUSION

The data shown herein demonstrate that the peptide SVH1C (NPSHPLSG, SEQ ID NO:3), functionally mimic glycans with terminal Neu5Ac-Gal sequences. Receptors such as NKG2D and siglecs bind these glycans. Siglec-1 is expressed on monocytes and macrophages and is involved in cellular adhesion but also enhances endocytosis of viruses [38,39]. Therefore, these peptides should function as modulators of cell activity by serving as a ligand for these receptors.

Similarly, the data shown herein demonstrate that the peptide SV6D (NQHTPR, SEQ ID NO:5), functionally mimic glycans with terminal N-acetylgalactosamine or galactose residues. Receptors such as CLEC10a and ASGPR-1 bind these glycans. CLEC10a is expressed on immature dendritic cells and macrophages and enhances endocytosis [22,24]. Therefore, these peptides should function as modulators of cell activity by serving as a ligand for these receptors.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

REFERENCES

1. Qu J-H, Chang X-J, Lu Y-Y, Bai W-L, Chen Y, Zhou L, and 9 co-authors. 2012. Overexpression of metastasis-associated in colon cancer 1 predicts a poor outcome of hepatitis B virus-related hepatocellular carcinoma. World J Gastroenterol 18:2995-3003.
2. Miyauchi K, Kim Y, Latinovic O, Morozov V, Melikyan G B. 2009. HIV enters cells via endocytosis and dynamic-dependent fusion with endosomes. Cell 137:433-444.
3. Choudhary S K, Margolis D M. 2011. Curing HIV: Pharmacologic approaches to target HIV-1 latency. Annu Rev Pharmacol Toxicol 51:397-418.
4. Davey R T, Bhat N, Yoder C, and 17 co-authors. 1999. HIV-1 and T cell dynamics after interruption of highly active antiretroviral therapy (HAART) in patients with a history of sustained viral suppression. Proc Natl Acad Sci USA 96:15109-15114.
5. US Food and Drug Administration. May 23, 2011. Approval of Victrelis (boceprevir), a direct acting antiviral drug (DAA) to treat hepatitis C virus (HCV); Approval of Incivek (telaprevir), a direct acting antiviral drug (DAA) to treat hepatitis C virus (HCV).
6. Pollicino T, Koumbi L. 2015. Role natural killer group 2D-ligand interactions in hepatitis B infection. World J Hepatol 7:819-824.
7. Leenders M W H, Nijkamp M W, Borel Rinkes I H M. 2008. Mouse models in liver cancer research: a review of current literature. World J Gastroenterol 14>6915-6923.
8. Yeh M M, Yeung R S, Apisarnthanarax S, Bhattacharya R, Cuevas C, Harris W P, Hon T L H, Padia S A, Park J O, Riggle K M, Daoud S S. 2015. Multidisciplinary perspective of hepatocellular carcinoma: a Pacific Northwest experience. World J Hepatol 7:1460-1483.
9. "Cancer," World Health Organization, February 2006.
10. Eggink L L, Hoober J K. 2009. A biologically active peptide mimetic of N-acetylgalactosamine/galactose. BMC Res Notes 2:23.
11. Yi J S, Du M, Zajac A J. 2009. A vital role for interleukin-21 in the control of chronic viral infection. Science 324:1572-1576.
12. Elsaesser H, Sauer K, Brooks D G. 2009. IL-21 is required to control chronic viral infections. Science 324: 1569-1572.
13. Macauley M S, Crocker P R, Paulson J C. 2014. Siglec-mediated regulated of immune cell function in disease. Nature Rev Immunol 14: 653-666.
14. Jellusova J, Nitschke L. 2012. Regulation of B cell functions by the sialic acid-binding receptors Siglec-G and CD22. Front Immunol 2: Article 96.
15. Pillai S, Netravali I A, Cariappa A, Mattoo H. 2012. Siglecs and immune regulation. Annu Rev Immunol 30; 357-392.
16. Prescher H, Schweizer A, Kuhfeldt E, Nitschke L, Brossmer R. 2014. Discovery of multifold modified sialosides as human CD22/Siglec-2 ligands with nanomolar activity on B-cells. ACS Chem Biol 9: 1444-1450.
17. Raulet D H. 2003. Roles of the NKG2D immunoreceptor and its ligands. Nature Rev Immunol 3:781-790.
18. Imaizumi Y, Higai K, Suzuki C, Azuma Y, Matsumoto K. 2009. NKG2D and CD94 bind to multimeric $\alpha$2,3-linked N-acetylneuraminic acid. Biochem Biophys Res Commun 382:604-608.
19. Eggink L L, Hoober J K. 2010. Peptide mimetics of terminal sugars of complex glycans. Glycobiol Insights 2:1-12.
20. Geijtenbeek T B H, Gringhuis S I. 2009. Signalling through C-type lectin receptors: shaping immune responses. Nature Rev Immunol 9:465-479.
21. Garcia-Vallejo J J, van Kooyk Y. 2009. Endogenous ligands for C-type lectin receptors: the true regulators of immune homeostasis. Immunol Rev 230:22-37.
22. van Vliet S J, Saeland E, van Kooyk Y. 2008. Sweet preferences of MGL: carbohydrate specificity and function. Trends Immunol 29:83-90.
23. Trowbridge I S, Thomas M L. 1994. CD45: an emerging role as a protein tyrosine phosphatase required for lymphocyte activation and development. Annu Rev Immunol 12:85-116.
24. Van Kooyk Y, Ilarregui J M, van Vliet S J. 2015. Novel insights into the immunomodulatory role of the dendritic cell and macrophage-expressed C-type lectin MGL. Immunobiology 220:185-192.
25. Degli-Esposti M A, Smyth M J. 2005. Close encounters of different kinds: dendritic cells and N K cells take centre stage. Nat Rev Immunol 5:112-124.
26. van Vliet S J, Gringhuis S I, Geijtenbeek T B H, van Kooyk Y. 2006. Regulation of effector T cells by antigen-presenting cells via interaction of the C-type lectin MGL with CD45. Nature Immunol 7:1200-1208.
27. Yamamoto N, Naraparaju V R, Asbell S O. 1996. Deglycosylation of serum vitamin D3-binding protein leads to immunosuppression in cancer patients. Cancer Res 56:2827-2831.
28. Sharma P, Allison J P. 2015. Immune Checkpoint Targeting in Cancer Therapy: Toward Combination Strategies with Curative Potential. Cell 161:205-214
29. Champsaur M, Lanier L L. 2010. Effect of NKG2D ligand expression on host immune responses. Immunol Rev 235:267-285.
30. Bone H, Williams N A. 2001. Antigen-receptor cross-linking and lipopolysaccharide trigger distinct phosphoinositide 3-kinase-dependent pathways to NK-κB activation in primary B cells. Int Immunol 13:807-816.
31. Marsh C B, Lowe M P, Rovin B H, Parker J M, Liao Z, Knoell D L, Wewers M D. 1998. Lymphocytes produce IL-1beta in response to Fcgamma receptor cross-linking: effects on parenchymal cell IL-8 release. J Immunol 160:3942-3948.
32. Li P, Morris D L, Willcox B E, Steinle A, Spies T, Strong R K. 2001. Complex structure of the activating immunoreceptor NKG2D and its MHC class 1-like ligand MICA. Nature Immunol 2:443-451.
33. McFarland B J, Kortemme T, Yu S F, Baker D, Strong R K. 2003. Symmetry recognizing asymmetry: analysis of the interactions between the C-type lectin-like immunoreceptor NKG2D and MHC class 1-like ligands. Structure 11:411-422.
34. Feinberg H, Rowntree T J W, Tan S L W, Drickamer K, Weis W I, Taylor M E. 2013. Common polymorphisms in human langerin change specificity for glycan ligands. J Biol Chem 288:36762-36771.
35. Mammen M, Choi S-K, Whitesides G M. 1998. Polyvalent interactions in biological systems: implications for design and use of multivalent ligands and inhibitors. Angew Chem Int Ed 37:2754-2794.
36. Dimick S M, Powell S C, McMahon S A, Moothoo D N, Naismith J H, Toone E J. 1999. On the meaning of affinity: cluster glycoside effects and Concanavalin A. J Am Chem Soc 121:10286-10296.
37. Cairo C W, Gestwicki J E, Kanai M, Kiessling L L. 2002. Control of multivalent interactions by binding epitope density. J Am Chem Soc 124:1615-1619.
38. Rempel H, Calosing C, Sun B, Pulliam L. 2008. Sia-loadhesin expressed on IFN-induced monoctes binds HIV-1 and enhances infectivity. PLoS ONE 3(4):e1967.
39. Zou Z, Chastain A, Moir S and 7 co-authors. 2011. Siglecs facilitate HIV-1 infection of macrophages through adhesion with viral sialic acids. PLoS ONE 6(9):e24559.
40. Angata T, Tabuchi Y, Nakamura K, Nakamuras M. 2007. Siglec-15: an immune system Siglec conserved throughout vertebrate evolution. Glycobiology 17:838-846.
41. Spiro R G, Bhoyroo V D. 1974. Structure of the O-glycosidically linked carbohydrate units of fetuin. J Biol Chem 249:5704-5717.
42. Baenziger J U, Fiete D. 1979. Structure of the complex oligosaccharides of fetuin. J Biol Chem 254:789-795.
43. Eggink L L, Salas M, Hanson C V, Hoober J K. 2010. Peptide sugar mimetics prevent HIV-1 replication in peripheral blood mononuclear cells in the presence of HIV-positive antiserum. AIDS Res Human Retrovir 26:149-160.
44. Michaelis M, Doerr H W, Cinatl J. 2009. The story of human cytomegalovirus and cancer: increasing evidence and open questions. Neoplasia. 2009 January; 11(1):1-9.

What is claimed is:

1. A method of treating a subject having cancer, a viral infection, or both, comprising administering to the subject a first therapeutic peptide or a first multivalent structured polypeptide comprising multiple copies of the first therapeutic peptide, wherein the first therapeutic peptide consists of 6 to 8 amino acids comprising NQHTPR (SEQ ID NO:5), and the first therapeutic peptide or first multivalent structured polypeptide is in an amount sufficient to treat the cancer, the viral infection, or both in the subject.

2. The method of claim 1, further comprising administering to the subject at least one agent selected from the group consisting of: an anti-inflammatory agent, a cytotoxic T cell proliferation agent, and an NK cell proliferation agent.

3. The method of claim 1, further comprising administering to the subject an antibody preparation admixed in an amount sufficient to enhance antibody-mediated cellular cytotoxicity in the subject or an immunoglobulin admixed in an amount sufficient to enhance passive immunoprotection in the subject.

4. The method of claim 1, further comprising administering to the subject a second therapeutic peptide or a second multivalent structured polypeptide comprising multiple copies of the second therapeutic peptide.

5. A therapeutic composition, comprising:
a first therapeutic peptide or a first multivalent structured polypeptide in an amount sufficient to treat cancer in a subject, wherein the first therapeutic peptide is comprises NQHTPR (SEQ ID NO:5), and the first multivalent structured polypeptide comprises multiple copies of the first therapeutic peptide; and at least one agent selected from the group consisting of: a B cell proliferative agent, a cytotoxic T cell proliferation agent, and an NK cell proliferation agent.

6. The therapeutic composition of claim 5, further comprising a carrier, and the at least one agent consists of a B cell proliferative agent and an NK cell proliferation agent.

7. The therapeutic composition of claim 5, further comprising a carrier, and the at least one agent consists of a cytotoxic T cell proliferation agent and an NK cell proliferation agent.

8. The therapeutic composition of claim 5, wherein the at least one agent consists of a B cell proliferative agent.

9. The therapeutic composition of claim 5, wherein the at least one agent consists of a cytotoxic T cell proliferation agent.

10. The therapeutic composition of claim 5, wherein the at least one agent consists of an NK cell proliferation agent.

11. The therapeutic composition of claim 5, further comprising an antibody preparation admixed in an amount sufficient to enhance antibody-mediated cellular cytotoxicity in the subject.

12. The therapeutic composition of claim 5, further comprising an immunoglobulin admixed in an amount sufficient to enhance passive immunoprotection in the subject.

13. The therapeutic composition of claim 5, further comprising a second therapeutic peptide or a second multivalent structured polypeptide comprising multiple copies of the second therapeutic peptide.

14. The method of claim 13, wherein the second therapeutic peptide is NPSHPLSG (SEQ ID NO:3).

15. The method of claim 1, wherein the subject has cancer and the first therapeutic peptide or first multivalent structured polypeptide is in an amount sufficient to treat the cancer in the subject, the first therapeutic peptide consists of N-Q-H-T-P-R-X7-X8 (SEQ ID NO: 13), and wherein X7 is S, L, or is absent, and X8 is G, or is absent.

16. The method of claim 15, wherein the first therapeutic peptide consists of NQHTPR (SEQ ID NO:5).

17. The method of claim 15, further comprising administering to the subject at least one agent selected from the group consisting of: an anti-inflammatory agent, a cytotoxic T cell proliferation agent, and an NK cell proliferation agent.

18. The method of claim 15, further comprising administering to the subject an antibody preparation admixed in an amount sufficient to enhance antibody-mediated cellular cytotoxicity in the subject or an immunoglobulin admixed in an amount sufficient to enhance passive immunoprotection in the subject.

19. The method of claim 1, wherein the subject has a viral infection and the first therapeutic peptide or first multivalent structured polypeptide is in an amount sufficient to treat the viral infection in the subject, the first therapeutic peptide consists of N-Q-H-T-P-R-X7-X8 (SEQ ID NO:13), and wherein X7 is S, L, or is absent, and X8 is G, or is absent.

20. The method of claim 19, further comprising administering to the subject a second therapeutic peptide or a second multivalent structured polypeptide comprising multiple copies of the second therapeutic peptide.

21. The method of claim 19, wherein the first therapeutic peptide consists of NQHTPR (SEQ ID NO:5).

22. The method of claim 21, further comprising administering to the subject at least one agent selected from the group consisting of: an anti-inflammatory agent, a cytotoxic T cell proliferation agent, an NK cell proliferation agent, an antibody preparation admixed in an amount sufficient to enhance antibody-mediated cellular cytotoxicity in the subject, an immunoglobulin admixed in an amount sufficient to enhance passive immunoprotection in the subject, a second therapeutic peptide, and a second multivalent structured polypeptide comprising multiple copies of the second therapeutic peptide.

23. The therapeutic composition of claim 5, wherein the first therapeutic peptide consists of N-Q-H-T-P-R-X7-X8 (SEQ ID NO:13), and wherein X7 is S, L, or is absent, and X8 is G, or is absent.

24. The therapeutic composition of claim 23, further comprising a second therapeutic peptide, or a second multivalent structured polypeptide comprising multiple copies of the second therapeutic peptide, wherein the first therapeutic peptide consists of NQHTPR (SEQ ID NO:5).

* * * * *

```
                          SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 1

Val Gly Gly Gly Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 2

His Pro Ser Leu Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 3

Asn Pro Ser His Pro Leu Ser Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 4

Asn Pro Ser His Pro Ser Leu Gly
1               5

<210> SEQ ID NO 5
<211> LENGTH: 6
<212> TYPE: PRT
```

```
<213> ORGANISM: Artificial Sequence
<220> FEATURE:
<223> OTHER INFORMATION: Synthetic Sequence

<400> SEQUENCE: 5

Asn Gln His Thr Pro Arg
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 6

Gly Gly Gly Ser
1

<210> SEQ ID NO 7
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 7

Gly Gly Gly Ser Gly Gly Gly Ser
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 8

Ser Ser Ser Ser
1

<210> SEQ ID NO 9
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 9

Ser Ser Ser Ser Ser Ser Ser Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 10

His Pro Ser Leu Gly
1               5

<210> SEQ ID NO 11
<211> LENGTH: 5
<212> TYPE: PRT
<213> ORGANISM: Artificial Sequence
```

```
<220> FEATURE:
<223> OTHER INFORMATION: Synthetic Sequence

<400> SEQUENCE: 11

His Pro Ser Leu Leu
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 12

His Pro Ser Leu Ala
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: X
<222> LOCATION: (7)..(7)
<223> OTHER INFORMATION: X is equal to serine, leucine, or is absent.
<220> FEATURE:
<221> NAME/KEY: X
<222> LOCATION: (8)..(8)
<223> OTHER INFORMATION: X is equal to glycine or is absent.

<400> SEQUENCE: 13

Asn Gln His Thr Pro Arg Xaa Xaa
1               5
```